(12) United States Patent
Kashiwagi

(10) Patent No.: US 6,458,113 B2
(45) Date of Patent: Oct. 1, 2002

(54) ABSORBENT ARTICLE

(75) Inventor: Masahiro Kashiwagi, Kagawa (JP)

(73) Assignee: Uni-Chem Corporation, Ehime (JP)

( * ) Notice: Subject to any disclaimer, the term of this patent is extended or adjusted under 35 U.S.C. 154(b) by 21 days.

(21) Appl. No.: 09/791,019

(22) Filed: Feb. 22, 2001

(30) Foreign Application Priority Data

Mar. 7, 2000 (JP) ...................................... 2000-062160

(51) Int. Cl.$^7$ .......................... A61F 13/15; A61F 13/20
(52) U.S. Cl. ......................... 604/385.16; 604/385.01; 604/358
(58) Field of Search ................... 604/358, 359–385.02, 604/385.03, 385.01, 385.04, 385.07–385.16, 385.22, 385.23–396, 397, 398–402, 317–357; 2/267, 268

(56) References Cited

U.S. PATENT DOCUMENTS

| | | | |
|---|---|---|---|
| 5,181,563 A | 1/1993 | Amaral | 604/385.2 |
| 5,584,829 A | 12/1996 | Lavash et al. | 604/387 |
| 5,730,738 A | 3/1998 | McFall et al. | 604/387 |
| 5,954,705 A | 9/1999 | Sawaki et al. | 604/385.1 |
| 6,193,701 B1 * | 2/2001 | Van Gompel et al. | 604/385.01 |

FOREIGN PATENT DOCUMENTS

| | | |
|---|---|---|
| EP | 0985396 A2 | 3/2000 |
| EP | 1132066 A1 | 9/2001 |
| JP | 4-164446 | 6/1992 |
| JP | 6-502336 | 3/1994 |
| JP | 7-33315 | 6/1995 |
| JP | 11-104168 | 4/1999 |
| WO | WO93/01786 | 2/1993 |
| WO | WO97/39710 | 10/1997 |
| WO | WO98/17217 | 4/1998 |
| WO | WO98/31320 | 7/1998 |

OTHER PUBLICATIONS

European Search Report.

* cited by examiner

Primary Examiner—Jeanette Chapman
(74) Attorney, Agent, or Firm—Darby & Darby

(57) ABSTRACT

There is disclosed an absorbent article including: a support body for confronting an external wear; a liquid absorbing member positioned on the liquid-receiving side of the support body; two side wall sheets disposed on two sides of the support body lying opposite one another in the widthwise direction, the side wall sheets being separated from one another in the widthwise direction and being longitudinally attached at their root ends to the support body; and a connecting sheet connecting the two side wall sheets. The side wall sheets are individually subjected to elastic shrinking forces in the longitudinal direction for shrinking to raise the free ends thereof from the support body to the liquid-receiving side, and the liquid absorbing member is supported by the connecting sheet so that the liquid absorbing member is movable over the support body while being unattached directly to the support body.

23 Claims, 24 Drawing Sheets

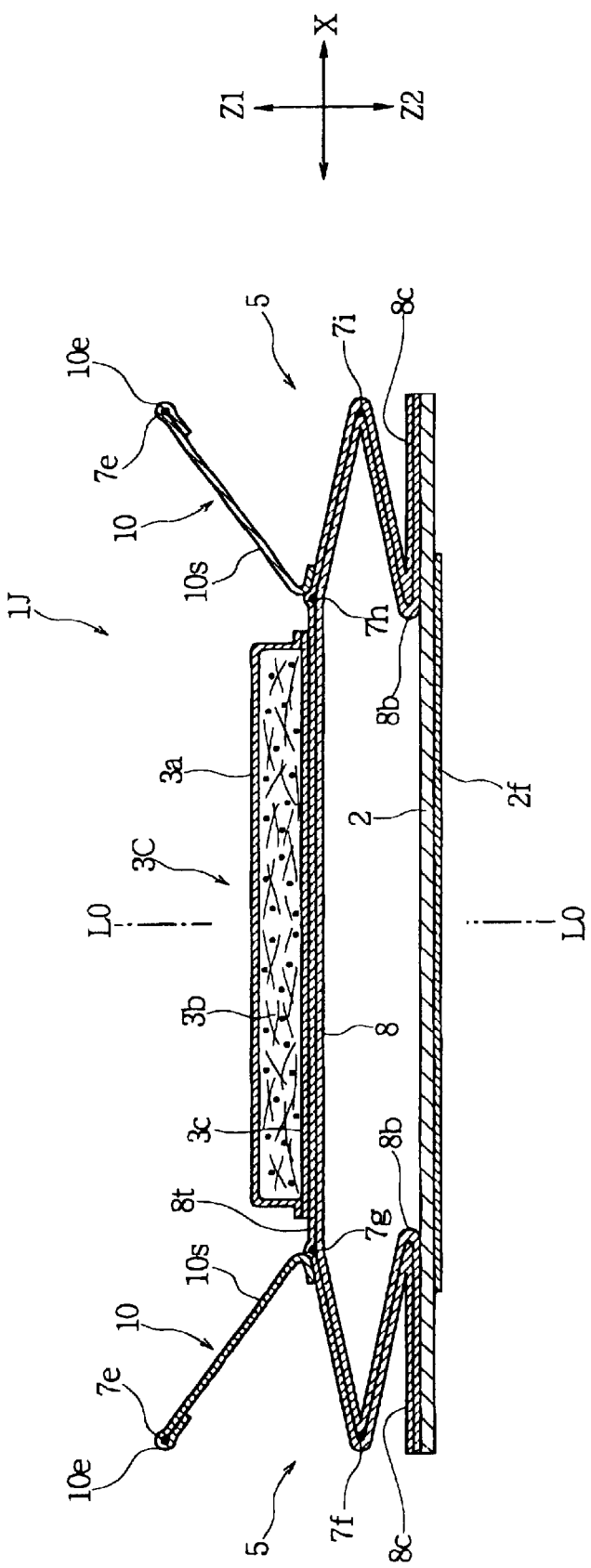

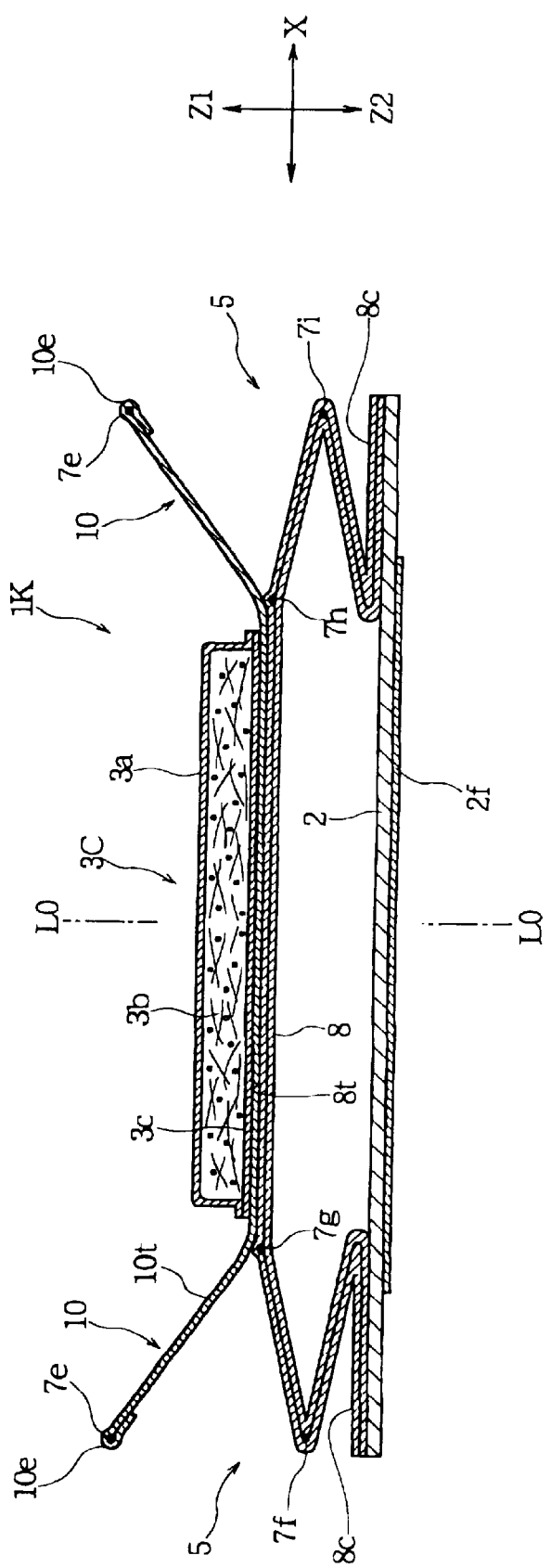

ABSORBENT ARTICLE

BACKGROUND OF THE INVENTION

1. Field of the Invention

The present invention relates mainly to an absorbent article for absorbing and retaining a liquid waste such as menstrual blood and, more particularly, to an absorbent article enabled to absorb the liquid waste effectively in accordance with the motions of a wearer.

2. Related art

In the prior art, there have been a variety of absorbent articles including a sanitary napkin, a pantie liner, a urine absorbing pad and a diaper. These absorbent articles are demanded, when worn, for absorbing the liquid waste reliably in an absorbent core so that the liquid waste may not leak to the outside of the absorbent articles.

Here, the body portion around a discharging part especially around a vaginal opening is different in shape among the states in which the wearer stands, sits down, or closes or opens legs, and especially changes its shape every moment while the wearer is walking. At this walking time, the muscles of the right and left buttocks are displaced transversely or vertically by about 30 mm at the maximum with respect to the longitudinal direction of the body.

As the right and left thighs make motions to intersect each other, more specifically, the muscular tissues of the thighs repeat relaxations and tensions. Of these muscular tissues, the inguinal ligaments on the inner sides of the thigh portions are so associated with the movements of the thighs as to move within a predetermined range on the inner sides of the thighs.

At this time, the muscular tissues in the vicinities of the ligaments move so that the skin surfaces of those portions sink from the surrounding skin surfaces. This sinking phenomenon occurs for time so that it is caused to restore its original state by the relaxations of the muscular tissues. Where the relaxations/tensions of the thighs are intermittently repeated as at the walking time, the sinking phenomenon also occurs intermittently. This sinking phenomenon occurs not only at the walking time but also at the time of opening/closing the legs or at the time of shifting the sleeping positions. This sinking portion fails to come into close contact with an absorbent core of the absorbent article so that a clearance is frequently established to leak the liquid waste from the clearance.

As the sanitary napkin to be brought into contact with the discharging part, a sanitary napkin, in which an absorbent core can move from a liquid-impermeable back sheet toward a wearer, is disclosed in International Unexamined Patent Publication No. 6-502336 (i.e., WO92/07535), for example. In Unexamined Published Japanese Patent Application No. 4-164446, on the other hand, there is disclosed a sanitary napkin which is provided with an upper absorber over a lower absorber. In these napkins, the upper absorbent core can easily come into close contact with the recess of the discharging part to prevent the leakage better than the ordinary napkin. In these napkins, however, the motions of the wearer cannot be followed to establish a clearance from the recessed portion.

In Unexamined Published Japanese Utility Model Application No. 7-33315, there is disclosed an absorbent article (or a sanitary napkin) which aims at preventing the leakage of a menstrual blood even when the wearer freely moves around. This absorbent article includes an upper napkin and a lower napkin, of which the smaller upper napkin is positioned at the central portion of the larger lower napkin whereas this lower napkin is attached to a pair of (i.e., righthand and lefthand) elastic members extending longitudinally from the two end portions of the upper napkin. These upper napkin and lower napkin can move relatively freely without restraining each other. A similar technique is disclosed in Unexamined Published Japanese Patent Application No. 11-104168.

In the napkin of the above-specified Application, the upper napkin can come reliably into close contact with the discharging part when the wearer stands upright. However, the upper napkin is always tensed forward and backward by the elastic members extending forward and backward from the two end portions of the upper napkin and connecting the upper napkin and the lower napkin. Therefore, the upper napkin can not move forward or backward freely and independently of the lower napkin. As a result, in the case where the lower napkin being applied to an underwear is deformed to have one side potion forward and to have the other side portion backward due to the opposite motions of the right and left legs as the wearer walks, the upper napkin being close contact with the discharging part will be influenced by the deformation of the lower napkin to cause a twist. Therefore, a clearance is established between the discharging part and the upper napkin so that the leakage occurs.

SUMMARY OF THE INVENTION

The invention has an object to provide an absorbent article which is excellent in the followability to the motions of a wearer while keeping a high contact with a discharging part.

According to a first aspect of the invention, there is provided an absorbent article comprising: a support body for confronting an external wear; a liquid absorbing member positioned on the liquid-receiving side of the support body; two side wall sheets disposed on two sides of the support body lying opposite one another in the widthwise direction, the side wall sheets being separated from one another in the widthwise direction and being longitudinally attached at their root ends to the support body; and a connecting sheet connecting the two side wall sheets, wherein the side wall sheets are individually subjected to elastic shrinking forces in the longitudinal direction for shrinking to raise the free ends thereof from the support body to the liquid-receiving side, and the liquid absorbing member is supported by the connecting sheet so that the liquid absorbing member is movable over the support body while being unattached directly to the support body.

According to the first aspect of the invention, the liquid absorbing member is supported while floating from the support body by the connecting sheet extending between the side wall sheets (or side walls formed therefrom to rise to a wearer), so that the liquid absorbing member can move freely and independently of the support body in a proper moving range in the longitudinal and widthwise directions over the support body. Moreover, the side walls on the right and left sides of the liquid absorbing member can move relatively independently from each other. In addition, the liquid absorbing member is not attached directly to the side walls but is attached indirectly (or connected) through the connecting sheet to the side walls. Even if the liquid absorbing member is deformed, therefore, the deformation force is hardly applied to the side walls so that the shape of the side walls rising to the liquid-receiving side is hardly destroyed. As a result, the liquid absorbing member can fit reliably on the discharging part even when a wearer moves so that little liquid waste such as menstrual blood leaks. In addition, due to its followability to the motions of a wearer, the liquid absorbing member is prevented from being rubbed against the skin of a wearer harshly so that a comfortable wearing feel can be achieved.

It is preferred that the connecting sheet has a stretchability in the longitudinal direction.

The liquid absorbing member may include an absorbent core and a liquid-permeable sheet covering at least the liquid-receiving side surface of the absorbent core, and may be attached to the liquid-receiving side surface of the connecting sheet. Alternatively, the connecting sheet may be liquid-permeable, and the liquid absorbing member may be attached to the support body-facing side surface of the connecting sheet.

It is preferred that longitudinal front and rear end portions of the side wall sheets are wholly attached to the support body to exert forces to curve the support body in the longitudinal direction so that the liquid-receiving side is recessed.

For exhibiting the elastic shrinking forces in the longitudinal direction, the sidewall sheets may be formed with corrugations repeated in the longitudinal direction and/or elastic members may be attached to the side wall sheets.

In the case where the elastic members are provided, each side wall sheet may be provided with a plurality of elastic members extending in the longitudinal direction and arranged at a spacing therebetween from the root end to the free end.

The side wall sheets may extend in a zigzag shape or a corrugated shape from the root ends to the free ends.

The connecting sheet may be attached to the side wall sheets respectively at a position between the free end and the root end, and the side wall sheets may be extended at their free ends farther toward the liquid-receiving side than the attached portions to the connecting sheet so that leakage preventing cuffs may be formed of the extensions of the side wall sheets from the attached portions. Alternatively, it is also possible to provide leakage preventing cuffs separately of the side wall sheets.

In the case where leakage preventing cuffs are formed of the extensions of the side wall sheets, it is preferred that elastic members are attached to the free ends of the side wall sheets for exhibiting elastic shrinking forces in the longitudinal direction.

Another absorbent member may be provided on the support body to confront the liquid absorbing member supported by the connecting sheet.

According to a second aspect of the invention, there is provided an absorbent article comprising: a support body for confronting an external wear; a liquid absorbing member positioned on the liquid-receiving side of the support body; and a side wall sheet having two side portions and a central portion therebetween in the widthwise direction, the side wall sheet connecting two side portions of the support body lying opposite one another in the widthwise direction, with its two side portions being individually attached to the two side portions of the support body but with its central portion being unattached to the support body, wherein the side wall sheet is subjected to an elastic shrinking force in the longitudinal direction for shrinking to separate its central portion from the support body to the liquid-receiving side, and the liquid absorbing member is supported by the central portion of the side wall sheet so that the liquid absorbing member is movable over the support body while being unattached directly to the support body.

The absorbent article according to the second aspect of the invention can also achieve the same functions and effects as those of the absorbent article according to the first aspect of the invention.

It is preferred that the side wall sheet has a stretchability in the longitudinal direction.

The liquid absorbing member may include an absorbent core and a liquid-permeable sheet covering at least the liquid-receiving side surface of the absorbent core, and may be attached to the liquid-receiving side surface of the central portion of the side wall sheet. Alternatively, the side wall sheet-may be liquid-permeable, and the liquid absorbing member may be attached to the support body-facing side surface of the central portion of the side wall sheet.

It is preferred that longitudinal front and rear end portions of the side wall sheet are wholly attached to the support body to exert a force to curve the support body in the longitudinal direction so that the liquid-receiving side is recessed.

For exhibiting the elastic shrinking force in the longitudinal direction, the side wall sheet may be formed with corrugations repeated in the longitudinal direction and/or elastic members may be attached to the side wall sheet.

In the case where the elastic members are provided, each side portion of the side wall sheet may be provided with a plurality of elastic members extending in the longitudinal direction and arranged at a spacing therebetween toward the central portion of the side wall sheet.

The side portions of the side wall sheet may extend in a zigzag shape or a corrugated shape toward the central portion of the side wall sheet.

Leakage preventing cuffs may be provided on two widthwise sides of the liquid absorbing member to rise toward the liquid-receiving side.

Another absorbent member may be provided on the support body to confront the liquid absorbing member supported by the central portion of the side wall sheet.

BRIEF DESCRIPTION OF THE DRAWINGS

FIG. 23 is a sectional view taken along line XXIII—XXIII of FIG. 22; and

FIG. 24 is a sectional view showing a modification of the sanitary napkin of the fourth embodiment.

DESCRIPTION OF THE PREFERRED EMBODIMENTS

Figure 1:
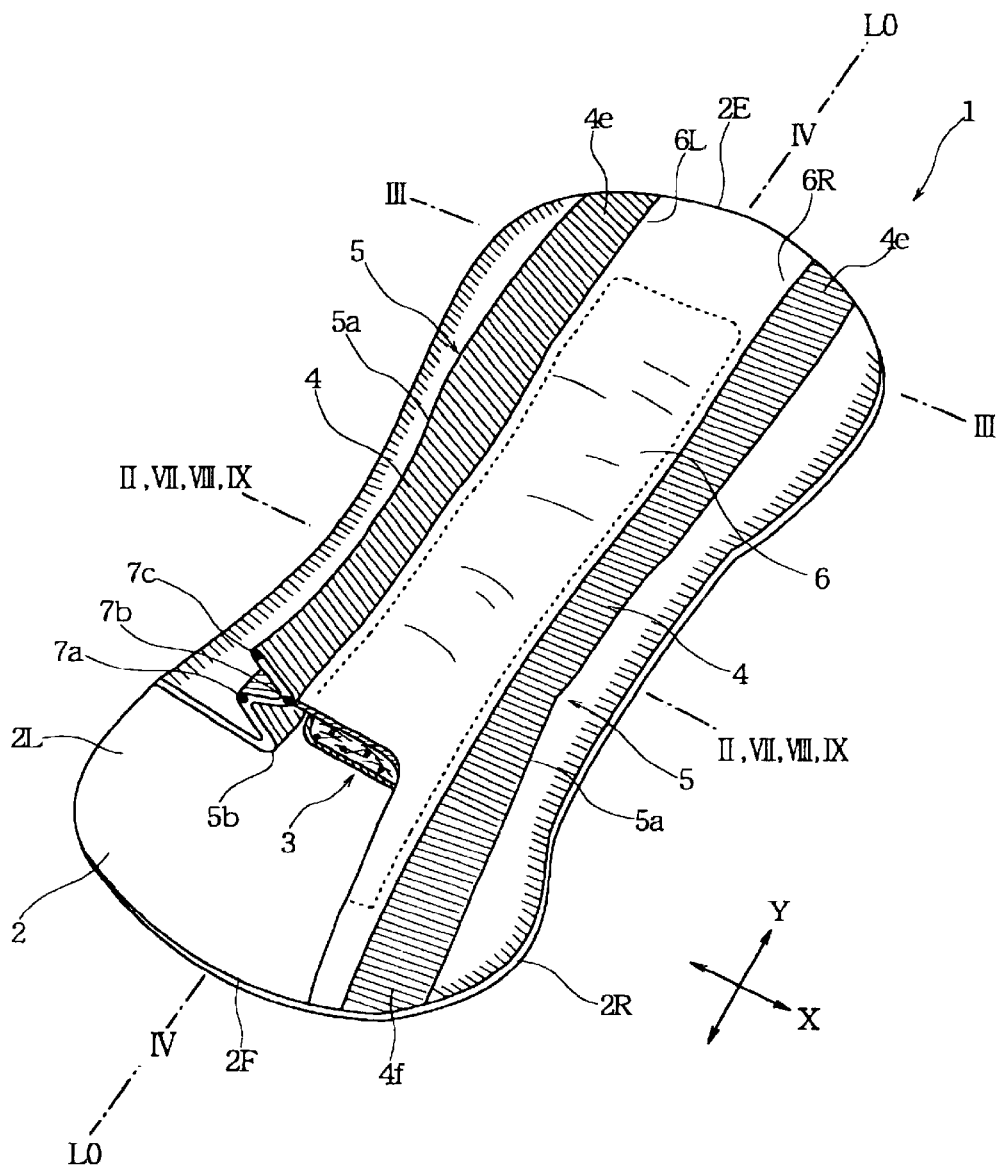
FIG. 1 is a partially sectioned perspective view showing a sanitary napkin as an absorbent article according to a first embodiment of the invention.
Figure 2:
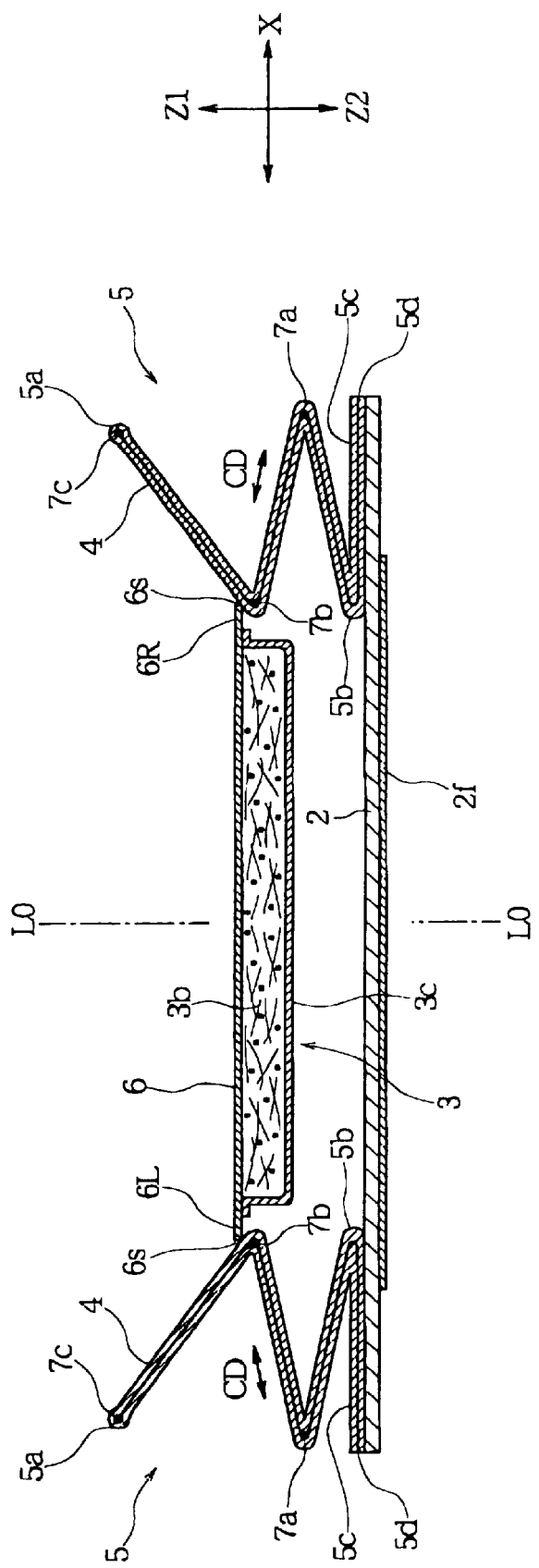
FIG. 2 is a sectional view taken along line II—II of the sanitary napkin shown in FIG. 1.
Figure 3:
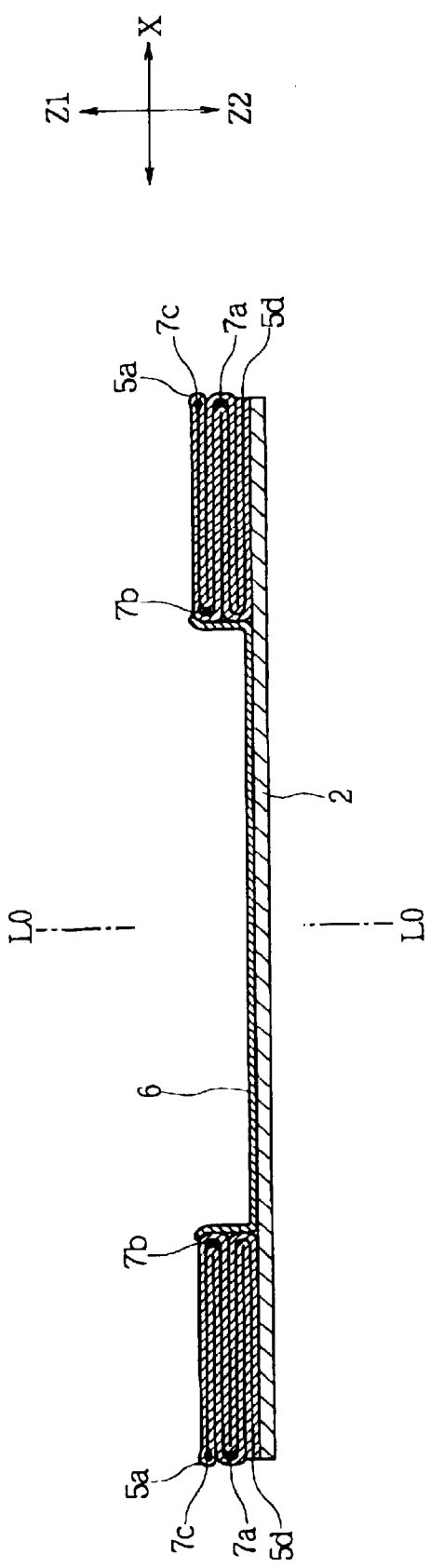
FIG. 3 is a sectional view taken along line III—III of FIG. 1.
Figure 4:
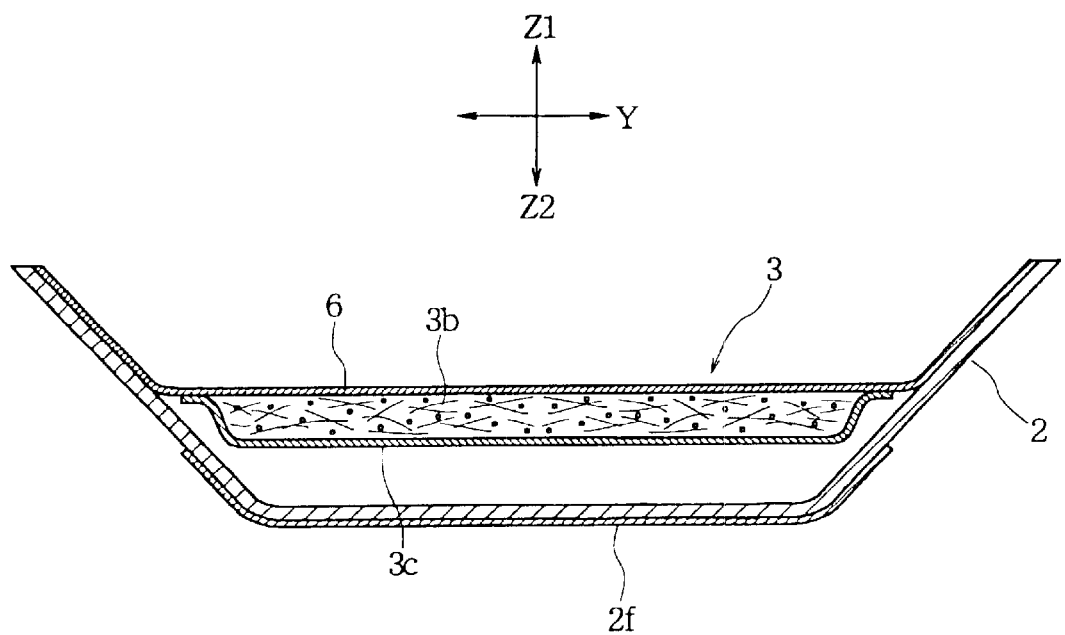
FIG. 4 is a sectional view taken along line IV—IV of FIG. 1.
Figure 7:
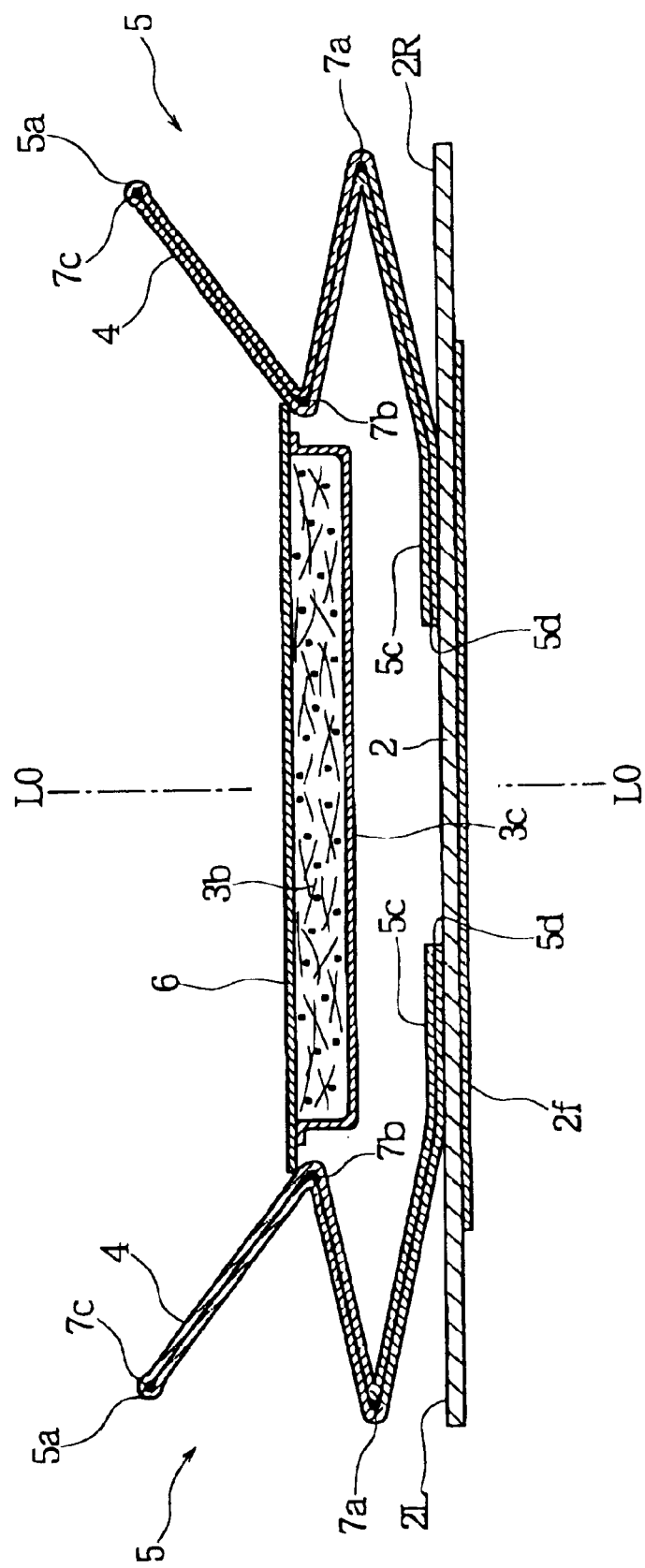
FIG. 7 is a sectional view showing a modification of the sanitary napkin of the first embodiment.
Figure 8:
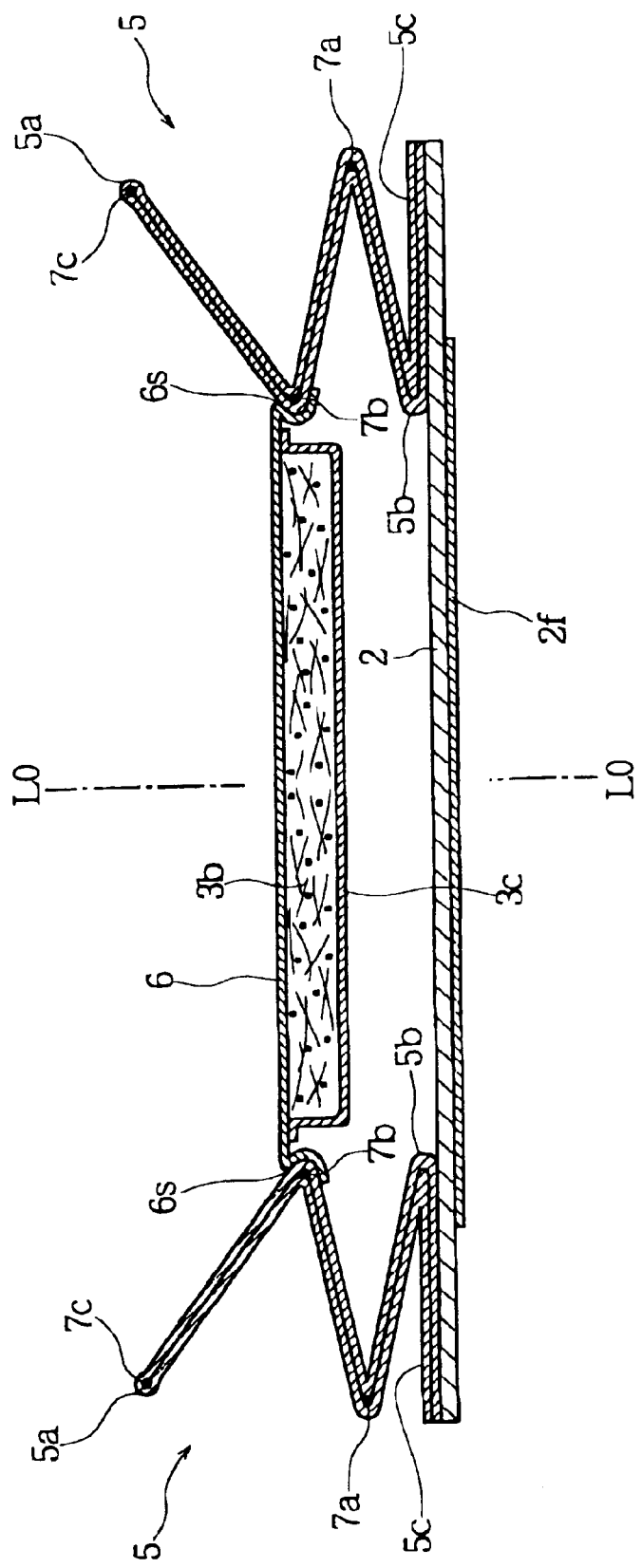
FIG. 8 is a sectional view showing another modification of the sanitary napkin of the first embodiment.
Figure 9:
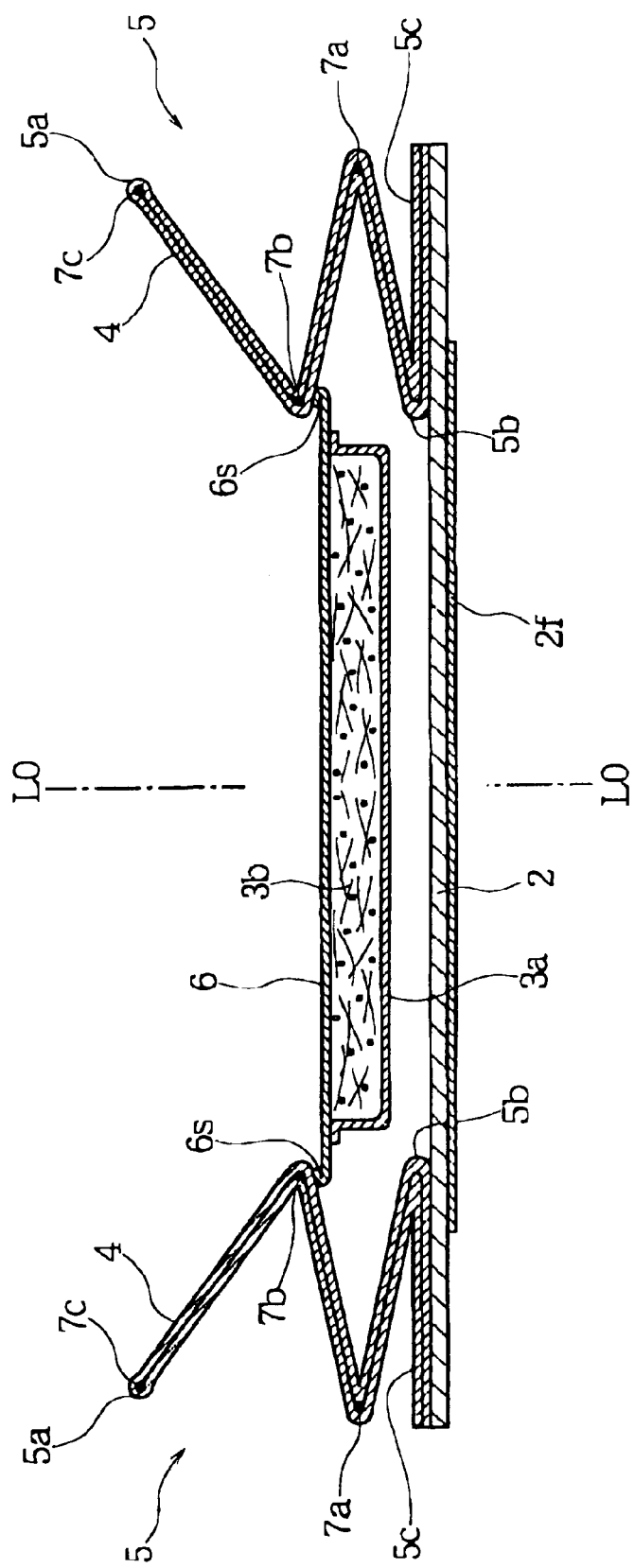
FIG. 9 is a sectional view showing still another modification of the sanitary napkin of the first embodiment.

The invention will be described with reference to the accompanying drawings. FIG. 1 is a partially sectioned perspective view taken from a liquid-receiving side and shows a sanitary napkin as an absorbent article according to a first embodiment of the invention; FIG. 2 is a sectional view taken along line II—II of FIG. 1; FIG. 3 is a sectional view taken along line III—III of FIG. 1; and FIG. 4 is a sectional view taken along line IV—IV of FIG. 1. FIGS. 7, 8 and 9 show modifications of the sanitary napkin of the FIG. 2, respectively. In these Figures: a direction X is taken in the widthwise direction (or transverse direction); a direction Y is taken in the longitudinal direction; and a direction Z1-Z2 is taken in the vertical direction (or height direction), in which the side indicated at Z1 is the liquid-receiving side (or the upper side) to face a discharging part of a wearer, whereas the side indicated at Z2 is the lower side to face an external wear such as underwear.

A sanitary napkin 1, as shown in FIG. 1, is constructed to mainly include: a support body 2 for facing the external wear such as underwear; a liquid absorbing member 3 located on the side of a wearer for absorbing a liquid waste; two side wall sheets 4 and 4 extending in the direction Y; and a connecting sheet 6 connecting the two side wall sheets 4 and 4. These side wall sheets 4 and 4 are disposed in the two side portions 2R and 2L of the support body 2 which extend in the direction Y and lie opposite one another in the widthwise direction. This sidewall sheet 4 is given a function to shrink in the direction Y so that it forms a side wall 5 with its free end 5a raised to the Z1 side, as shown in FIG. 2. The connecting sheet 6 is attached (or joined) at its two sides to the side walls 5 on the side closer to the free ends 5a. The liquid absorbing member 3 is attached to the lower surface (or the support body-facing side surface) of the connecting sheet 6. That is, the liquid absorbing member 3 is not attached directly to the support body 2 but is supported by the support body 2 through the connecting sheet 6 and the side wall sheets 4 and 4. In the unworn (or free) state, therefore, the liquid absorbing member 3 is positioned over the support body 2 at a spacing in the height direction (or the direction Z1-Z2), as shown in FIG. 2.

The support body 2 is preferably formed of a liquid-impermeable support sheet. This support sheet is made of an air-permeable resin film, a spun-bonded or spun-laced non-woven fabric made water-repellent, or a sheet prepared by joining an air-permeable resin film to the back of a non-woven fabric. The support body 2 is provided on its back with an adhesive layer 2f for retaining the support body 2 on an external wear such as underwear in use. Here, it is preferred that the adhesive layer 2f is covered with a release sheet for protecting it, till the sanitary napkin is used.

The side wall sheet 4 forming the side wall 5 is provided with fine wrinkles (or corrugations), which individually extend in the direction X, as shown in FIG. 1, and which are formed continuously and repeatedly in the direction Y. These wrinkles are formed such that a nonwoven fabric or the like forming side wall sheet 4 is heat-pressed to be corrugated.

Figure 5:
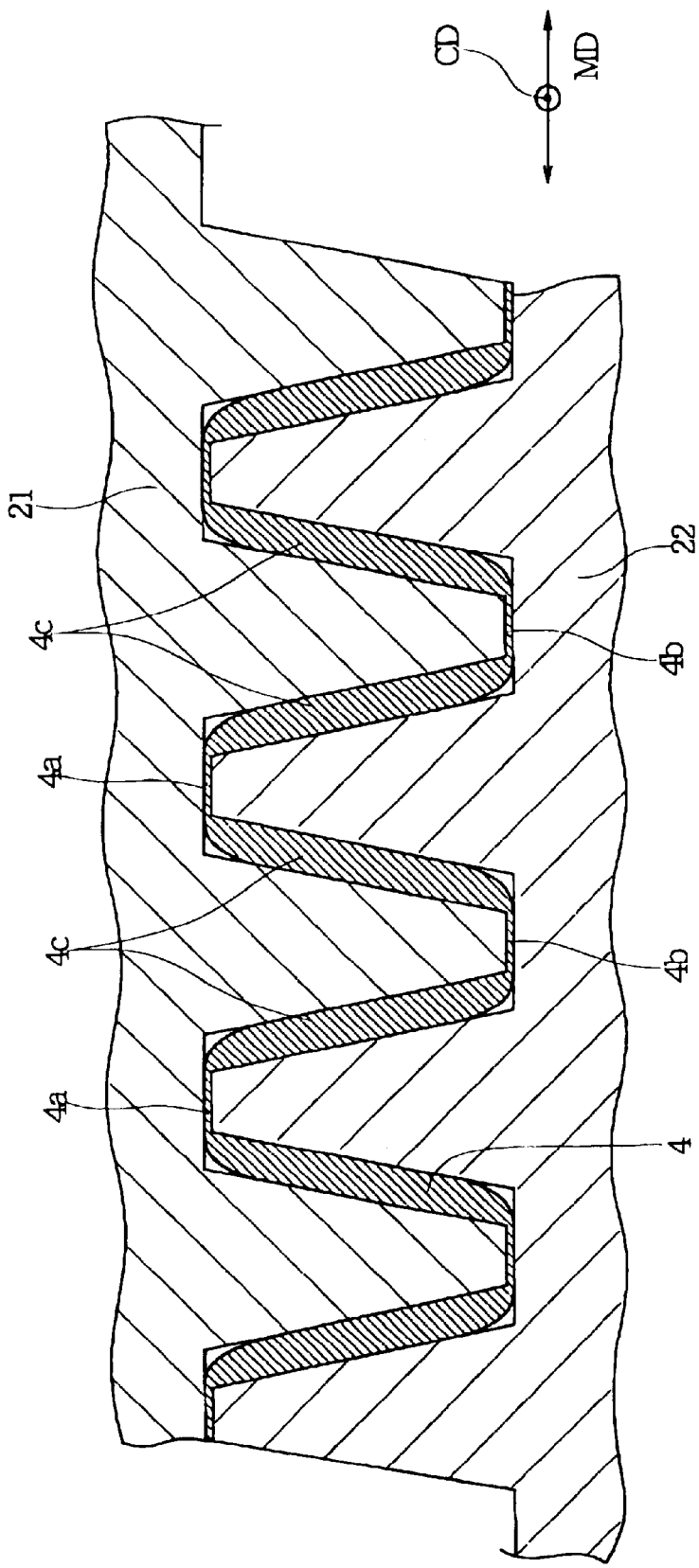
FIG. 5 is a sectional view of linear pressure molds and shows a pressing step of forming wrinkles in a side wall sheet.
Figure 6:
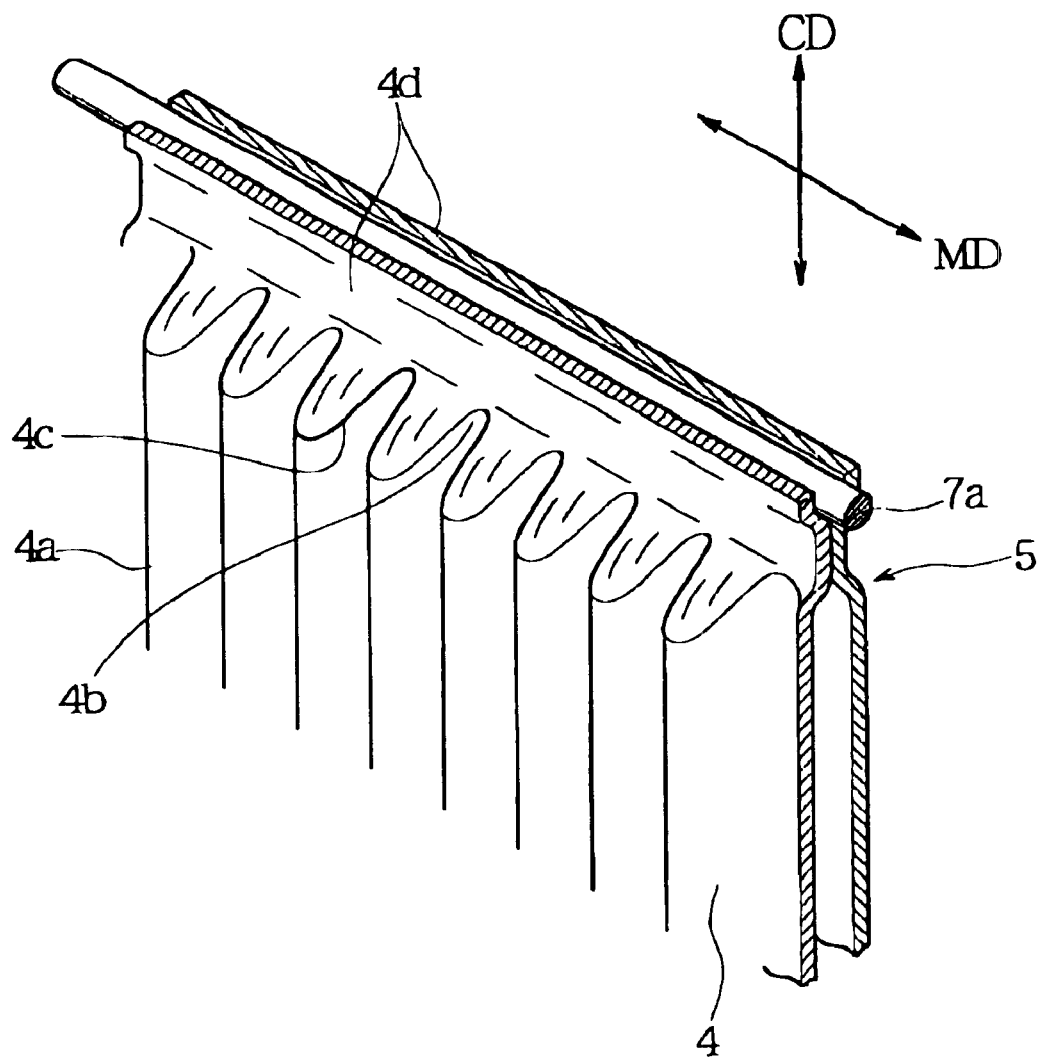
FIG. 6 is a perspective view showing a portion of the side wall sheet and an elastic member.

FIG. 5 is an explanatory diagram of the heat-pressing step, and FIG. 6 is a partially sectioned perspective view showing a portion of the side wall 5 of the heat-pressed sheet. At this heat-pressing step, the side wall sheet 4, which is formed of a nonwoven fabric formed only of or containing thermoplastic fibers such as a melt-blown nonwoven fabric, is heat-pressed between rolls. As shown in FIG. 5, the individual rolls have surfaces forming linear pressure molds 21 and 22. As the sheet is heated and pressed by the linear pressure molds 21 and 22, its fibers are compressed heavily at ridges 4a and valleys 4b and lightly at intermediate portions 4c. The side wall sheet 4 having passed the linear pressure molds 21 and 22 are corrugated to have the ridges 4a, the valleys 4b and the intermediate portions 4c extending individually in the Cross Direction (CD) and repeated and continued (or arranged) in the Machine Direction (MD), as shown in FIG. 6.

Since the side wall sheet 4 is corrugated, as shown in FIG. 6, it has an elastic stretchability in the MD along which the corrugations are arranged and a rich self-supportability and a high buckling strength in the CD along which the ridges 4a and the valleys 4b extend individually. This side wall sheet 4 is folded in two in the CD, as shown in FIG. 2, so that its fold (or crease) provides the free end 5a of the side wall 5 later.

The side wall sheet 4 for forming the side wall 5 of the invention is preferably shaped at the step shown in FIG. 5 into the wrinkled shape to have the elastic stretchability in the MD (or the direction Y) by itself. However, such an elastic stretchability in the direction Y may also be given to the side wall sheet 4 by other means. For example, the side wall sheet 4 may be formed of an elastically stretchable material such as a melt-blown nonwoven fabric of "SEPTON" (manufactured by KURARAY Co., Ltd.) or a sheet of urethane foam which has an elastic stretchability in the direction Y by itself, even when it is not corrugated at the step shown in FIG. 5. Alternatively, the side wall 5 may also be given an elastic stretchability in the direction Y by forming the side wall sheet 4 of a sheet not having a high elastic stretchability by itself, such as a spun-bonded nonwoven fabric, a point-bonded nonwoven fabric, an air-through nonwoven fabric, an air-laid nonwoven fabric, or a resin film of polyethylene (PE) or polypropylene (PP), and by attaching a yarn- or belt-shaped elastic members in the state elongated in the direction Y to the side wall sheet 4.

The side wall sheet 4 is preferably made hydrophobic or water-repellent. Where the side wall sheet 4 is formed of the nonwoven fabric, the fibers composing the nonwoven fabric are exemplified by the polyethylene (PE) fibers, polyethylene terephthalate (PET) fibers, or composite fibers such as PE/PP or PE/PET e.g., the core-sheath type fibers or side-by-side type fibers, which are made water-repellent. An alternative material can be a composite nonwoven fabric which is prepared by laminating the PE or PP on the nonwoven fabric. In addition, the hydrophobic sheet can be obtained by kneading the fibers with a surfactant having a hydrophobic group of a large molecular weight, a silicone compound such as dimethyl polysiloxane or a fluorochemical surfactant, or by applying the above-specified material to the surfaces of the fibers or the surface of nonwoven fabric. The hydrophobic sheet thus prepared can also be used as the side wall sheet 4.

In the embodiment shown in FIG. 2, the elastic stretchability in the direction Y is intensified by attaching elastic members, as elongated in the direction Y, to the elastically stretchable sheet which has the fine wrinkles formed at the step of FIG. 5. It should be noted that the sectional views such as FIGS. 2 and 3 have, for clarity, been simplified by the omission of the fine wrinkles shown in FIG. 6.

As shown in FIG. 2, more specifically, elastic members 7a, 7b and 7c are sandwiched between the two folded portions of the side wall sheet 4 and are adhered to side wall sheet 4 by a hot-melt adhesive or the like. The individual elastic members, as used herein, have such a free length (i.e., a length when no external force is applied) as is made substantially equal to or slightly shorter than that of the side wall sheet 4 having the wrinkles. After the sidewall sheet 4 is elongated in the MD (along which the wrinkles are arranged) so far as to generally flatten the wrinkles, the individual elastic members 7a, 7b and 7c are adhered to the generally flattened side wall sheet 4 while being elongated to the length equal to the elongated length of the side wall sheet 4. As a result, in the free state without any external force, the side wall sheet 4 is wrinkled and given an elastic stretchability in the direction Y. The adjoining elastic members shown in FIG. 2 have a spacing of 5 to 15 mm.

The elastic members 7a, 7b and 7c can be made of natural rubber, synthetic rubber, polyurethane or styrene-butadiene copolymer to take a shape of yarn, filament, film or band (or belt). Alternatively, the elastic members 7a, 7b and 7c may be prepared by cutting a stretchable nonwoven fabric such as an elastic spun-bonded nonwoven fabric or an elastic melt-blown nonwoven fabric.

The paired side wall sheets 4 and 4 thus provided with the elastic members are attached at their attachment portions 5c and 5c of a predetermined width to the two side portions 2R and 2L of the support body 2, while being elongated by about 1.2 to 1.8 times. At this time, trailing end portions 5d are directed to the outer sides of the support body 2 in the direction X. However, these attachment portions 7c may be formed with their trailing end portions 5d directed to the longitudinally extending center line L0 of the support body 2, as shown in FIG. 7.

It is preferred that the side walls 5 have a stretchable length within a range of 10 to 100% of its original length.

Below the lower limit, the side walls 5 are restricted in their motions to fail to follow the behaviors of the wearer. If the upper limit is exceeded, on the other hand, the shape of the side walls 5 is hardly retained. Moreover, it is preferred that the shrinking force of the side wall 5 (in the state where it is elongated to the limit) is 190 mN to 2,000 mN. The side walls 5 are hardly raised to the Z1 side, if the shrinking force is below the lower limit. If the upper limit is exceeded, the shrinking force is so high as to deteriorate the wearing feel.

As shown in FIG. 2, the side wall sheet 4 to be attached to the support body 2 is folded in a zigzag shape with the elastic members 7a, 7b and 7c being positioned at its apexes. In detail, the elastic member 7b is positioned on the side of the longitudinally extending center line L0 of the sanitary napkin 1, and the elastic members 7a and 7c are positioned on the outer side in the direction X of the sanitary napkin 1. At front and rear end portions 4e and 4f of the side wall sheet 4 in the direction Y, on the other hand, the side wall sheet 4 is folded flat in its entirety, as shown in FIG. 3, and are attached to front and rear end portions 2E and 2F of the support body 2.

The side wall 5 is elastically shrunken in the direction Y by the elastic shrinking force of the side wall sheet 4 itself forming the side wall 5 and by the elastic shrinking forces of the individual elastic members 7a, 7b and 7c. As a result, in the unworn state (or in the free state free from the external force), as shown in FIG. 4, the support body 2 is so curved in the direction Y as to recess the liquid-receiving side, and the side walls 5 rise in the zigzag shape from their root ends 5b and 5b to direct their free ends 5a and 5a to the Z1 side. It should be noted that FIG. 4 has been simplified by the omission of the side wall 5 in order to clarify the curved state of the support body 2.

Since the side wall sheets 4 are folded twice at the spacing between the elastic members, i.e., with a folding width of 5 to 15 mm, as shown in FIGS. 2 and 3, the side walls 5 can be softly deformed vertically (or in the direction Z1-Z2) when the sanitary napkin 1 is worn and the free ends 5a of the side walls 5 come into abutment against the skin of a wearer. Therefore, the side walls 5 can abut softly against the skin and can softly follow the motions of the wearer's body so that they can come into close contact with the skin at the free ends 5a and/or their peripheral regions thereby to hardly establish a clearance from the skin. In order that the side walls 5 may easily follow the motions of the wearer's body while being in close contact with the skin, it is preferred that the folding width of the side wall sheets is 5 to 15 mm and that the folding number is at least one, or preferably at least four. It should be noted that the folding positions of the side wall sheets 4 in the zigzag shape should not be limited to the portions where the elastic members are located. By forming the folds (or creases) at the portions where the elastic members are located, however, the side wall sheets 4 can be easily deformed into the zigzag shape, as shown in FIG. 2.

As shown in FIG. 6, the wrinkles are not formed all over the surface of the side wall sheet 4, but substantially flat portions 4d are formed at the portions where the elastic members 7a, 7b and 7c are attached. Then, the side wall sheet 4 can be easily folded into the zigzag shape, as shown in FIG. 2, along the portions where the elastic members are disposed.

For the sanitary napkin, the spacing between the two root ends 5b and 5b (i.e., between the root end 5b of the righthand side wall 5 provided in the righthand side portion 2R of the support body 2 and the root end 5b of the lefthand side wall 5 provided in the lefthand side portion 2L of the support body 2) in the direction X is preferably within a range of 30 mm to 100 mm. If the spacing is below the lower limit, the side walls 5 and 5 are located too close to each other. This results in reducing the width of the liquid absorbing member 3 existing inbetween. If the upper limit is exceeded, on the other hand, the spacing between the side walls 5 and 5 exceeds that of the crotch of the wearer to give an uncomfortable feel to the wearer when the sanitary napkin 1 is worn.

To the side walls 5 and 5 thus formed and raised in the direction Z1-Z2, the connecting sheet 6 is attached at its two side portions 6R and 6L. In the FIG. 2, the attached portions between the two side portions 6R and 6L of the connecting sheet 6 and the side walls 5 and 5 are indicated at 6s and 6s. These attached portions 6s and 6s are positioned closer to the free ends 5a in the side walls 5 and 5, more specifically, just above the elastic members 7b. The liquid absorbing member 3 is attached to the lower surface (or the support body-facing surface) of the connecting sheet 6. At the midway portion (or the central portion) of the sanitary napkin 1 in the direction Y, therefore, the liquid absorbing member 3 is lifted by the connecting sheet 6 so that it is supported at a position apart from the support body 2, as shown in FIG. 2.

At this time, the connecting sheet 6 may be attached to the side walls 5 with its side terminal ends directed to the support body 2, as shown in FIG. 8. In this structure, the connecting sheet 6 hardly makes a severe friction with the skin because its two side terminal ends never contact with the skin. On the other hand, it is preferable that the practical length (or the length in an unfolded state) of the portions of the side walls 5 extending from the attached portions 6s through the elastic members 7b and 7a to the root ends 5b is within a range of 10 mm to 50 mm. Within this range, the two side terminal ends of the connecting sheet 6 may be located at any positions of the side walls 5 such as just below the elastic members 7b, as shown in FIG. 9. Here, the two side terminal ends of the connecting sheet 6 are preferably attached to the zigzag side walls 5 in the vicinities of their ridges on the side of the longitudinally extending center line L0 (i.e., their inwardly protruding ridges) because the shape retaining property (or shape holdability) of the sidewalls 5 is enhanced.

The side wall sheet 4 forming the side wall 5, to which the connecting sheet 6 is attached, has the corrugated wrinkles individually extending in the CD, as shown in FIG. 6, so that it has a high buckling rigidity in the wrinkle extending direction (CD). As shown in FIG. 2, moreover, the side wall sheets 4 have the zigzag shape. Therefore, the connecting sheet 6 is supported on the two sides by the portions between the elastic members 7a and 7b of the side wall sheets 4, i.e., by the portions in which the wrinkles are extended from the elastic members 7a to the elastic members 7b. Therefore, the connecting sheet 6 is securely supported by the side walls 5 in such a manner that it is restricted within a moderately movable range but without moving largely to the right and left and that it is spaced away from the support body 2 while keeping a certain distance in the vertical direction. Since the side wall sheets 4 are raised vertically in the zigzag shape, moreover, the connecting sheet 6 can move relatively freely in the vertical direction (or in the direction Z1-Z2).

As a result, the liquid absorbing member 3. attached to the connecting sheet 6 is allowed, when the sanitary napkin 1 is worn, to move relatively freely over the support body 2 in accordance with the motion of the wearer s body. At this time, the right and left side walls 5 can be independently deformed. Even when the right and left crotch portions change in their shapes as the wearer walks, therefore, the right and left side walls 5 can easily follow the shape changes independently of each other. Moreover, the liquid absorbing member 3 is not attached directly to the side walls 5 but is connected through the connecting sheet 6 to the side walls 5. Even when the liquid absorbing member 3 is deformed while the sanitary napkin 1 is worn, therefore, the side walls 5 are hardly influenced by the deformation. On the other hand, the liquid absorbing member 3 is hardly dragged or deformed by the motions of the side walls 5. In the sitting or rising actions, therefore, a clearance is hardly established between the liquid absorbing member 3 and the skin of the wearer.

The liquid absorbing member 3 can move relatively freely over the support body 2, but its moving range is limited by the aforementioned practical length from the attached portions 6s to the root ends 5b. Moreover, the side walls 5 are so shaped as to hardly deform excessively to the right and left. Therefore, the liquid absorbing member 3 does not excessively move over the support body 2 out of the discharging part.

Since the side walls 5 are formed of the side wall sheets 4 having the wrinkles (or corrugations), they provide an excellent soft feel. With the wrinkles, moreover, the side walls 5 having been applied with an external force can be easily relaxed to allow the liquid absorbing member 3 to exhibit independent behaviors.

In the sanitary napkin 1, as has been described hereinbefore, the liquid absorbing member 3 can absorb the liquid waste so reliably as to prevent the liquid waste from leaking and blotting the underwear. Moreover, the support body 2 is curved in the direction Y, as shown in FIG. 4, by the shrinking forces of the side wall sheets 4 in the direction Y. As a result, the sanitary napkin 1 can better fit the crotch of the wearer.

In the sanitary napkin 1, the connecting sheet 6 is positioned slightly lower than the free ends 5a of the side walls 5 so that the extensions of the side walls 5 extending farther toward the Z1 side from the attached portions 6s of the connecting sheet 6 (that is, the portions from the attached portions 6s to the free ends 5a) exhibit the function of leakage preventing cuffs for preventing the liquid waste from leaking to the outside of the liquid absorbing member 3 in the direction X. In order to give the function of the leakage preventing cuffs to the side walls 5, the distance from the upper surface of the connecting sheet 6 to the free ends 5a of the side walls 5 is preferably no less than 5 mm or more preferably no less than 10 mm.

The connecting sheet 6 is preferably formed of a material stretchable in the direction Y. When the wearer steps back and forth to walk, forces opposed in the direction Y act on the righthand side portion 6R and the lefthand side portion 6L. In this case, if the connecting sheet 6 is stretchable in the direction Y, the righthand and lefthand side portions 6R and 6L are allowed to move oppositely in the direction Y (whereupon the connecting sheet 6 may take a generally parallelogram shape). Therefore, the liquid absorbing member 3 is not subjected to any excessive force so that it can be prevented from being deformed into an undesired shape or from excessively moving.

Here, it is preferable that the stretchability of the connecting sheet 6 is lower than that of the side walls. It is also preferable that the connecting sheet 6 has a stretchable length within a range of 20 to 200% of its original length. Below the lower limit, the liquid absorbing member 3 follows the motions of the side walls 5 completely to establish a clearance between the liquid absorbing member 3 and the discharging part. If the upper limit is exceeded, the connecting sheet 6 is stretched not to restore its original length so that it cannot push up the liquid absorbing member 3 from the support body 2 to the Z1 side.

On the other hand, the connecting sheet 6 is preferred to have no stretchability in the direction X or to have an extremely low stretchability in the direction X, if any. In other words, the connecting sheet 6 is preferred to have substantially no stretchability in the direction X. The stretch of the connecting sheet 6 in the direction X when the sanitary napkin 1 is worn causes an unnecessary movement of the liquid absorbing member 3 to establish the friction between the skin of the wearer and the liquid absorbing member 3; In addition, the side walls 5 having their free ends 5a raised to the Z1 side are collapsed to lose their functions as the leakage preventing cuffs.

The connecting sheet 6 can be made of an air-through nonwoven fabric, a spun-bonded nonwoven fabric, a spun-laced nonwoven fabric, a resin-bonded nonwoven fabric, an air-laid nonwoven fabric or a melt-blown nonwoven fabric, as formed by using synthetic fibers such as PE, PP, PET, polyurethane or nylon, natural fibers such as cellulose, cotton or rayon, etc. In an alternative, the connecting sheet 6 may be made of; a resin sheet formed of a thermoplastic resin such as PE, PP or PET; a resin sheet opened to have a low Young's modulus; or a mesh material having a knitted coarse structure such as a mandarin orange packaging net. It is also possible to form the connecting sheet 6 by combining a plurality of sheets. For example, the two side portions 6R and 6L of the connecting sheet 6 can be made of an opened sheet or mesh material, whereas the intermediate portions between the two side portions 6R and 6L can be made of the aforementioned nonwoven fabric or the like.

The liquid absorbing member 3 is attached to the support body-facing side surface of the connecting sheet 6 thus far described. In this structure, therefore, the connecting sheet 6 is formed of a liquid-permeable material so that it may transmit the waste liquid to the liquid absorbing member 3.

This liquid absorbing member 3 is formed, as shown by dotted lines in FIG. 1, into a rectangular shape one size smaller than the support body 2. The liquid absorbing member 3 may also be formed into the so-called "hour glass" shape or any other shapes. This liquid absorbing member 3 is constructed to include: an absorbent core 3b positioned just below the liquid-permeable connecting sheet 6; and a liquid-impermeable layer 3c covering the absorbent core 3b on the support body-facing side. This liquid-impermeable layer 3c is attached to the connecting sheet 6 in the periphery of the absorbent core 3b.

The absorbent core 3b is formed of pulverized pulp or a mixture of pulverized pulp and a highly water-absorbing polymer (or super absorbent polymer), by enveloping either the pulverized pulp or the mixture of the pulverized pulp and the highly water-absorbing polymer by an absorbent sheet or a liquid-permeable sheet such as tissue paper. In order to fit the liquid absorbing member 3 better on the discharging part, the absorbent core 3b is preferred to have an elastic deformability. In order to make the absorbent core 3b elastically deformable, the pulverized pulp and the highly water-absorbing polymer may contain pulverized urethane foam, pulverized cellulose sponge, air-rich materials of ball-shaped fibrous lumps, a laminate of a resin such as SEPTON formed into a net shape and having a stretchability, crimped fibers, or split yarns. These materials are preferably hydrophilic per se or subjected to hydrophilic treatment.

In order to enhance the liquid absorption of the absorbent core 3b, it is preferable to make the density of the absorbent core 3b higher toward the Z2 side. In this case, the liquid waste given to the absorbent core 3b through the connecting sheet 6 easily migrates toward the support body 2 in the absorbent core 3b to raise the absorbing rate and the absorption. Alternatively, two absorbing members may be laminated to form the absorbent core 3b such that the density of the lower layer (or the absorbing member on the support body-facing side) is higher than that of the upper layer (or the absorbing member on the liquid-receiving side).

The connecting sheet 6 and the absorbent core 3b are adhered by an olefin- or rubber-based hot melt adhesive. The application of the hot melt adhesive is performed, for example, in a comb-, spray- or spiral-pattern to prevent the liquid permeability from lowering between the connecting sheet 6 and the absorbent core 3b.

The liquid-impermeable layer 3c is made of an air-permeable resin film, or a spun-bonded or spun-laced nonwoven fabric made water-repellent.

Figure 10:
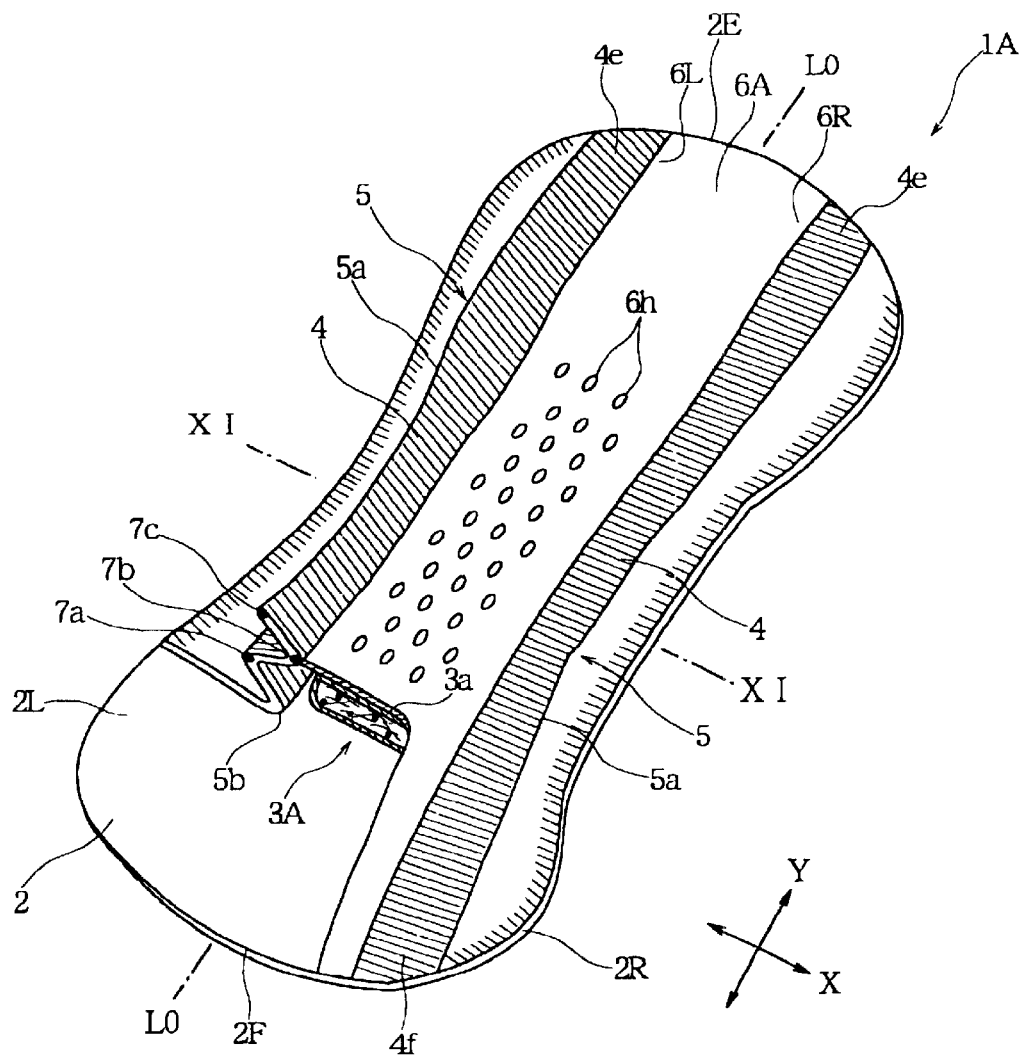
FIG. 10 is a partially sectioned perspective view showing a further modification of the sanitary napkin of the first embodiment.
Figure 11:
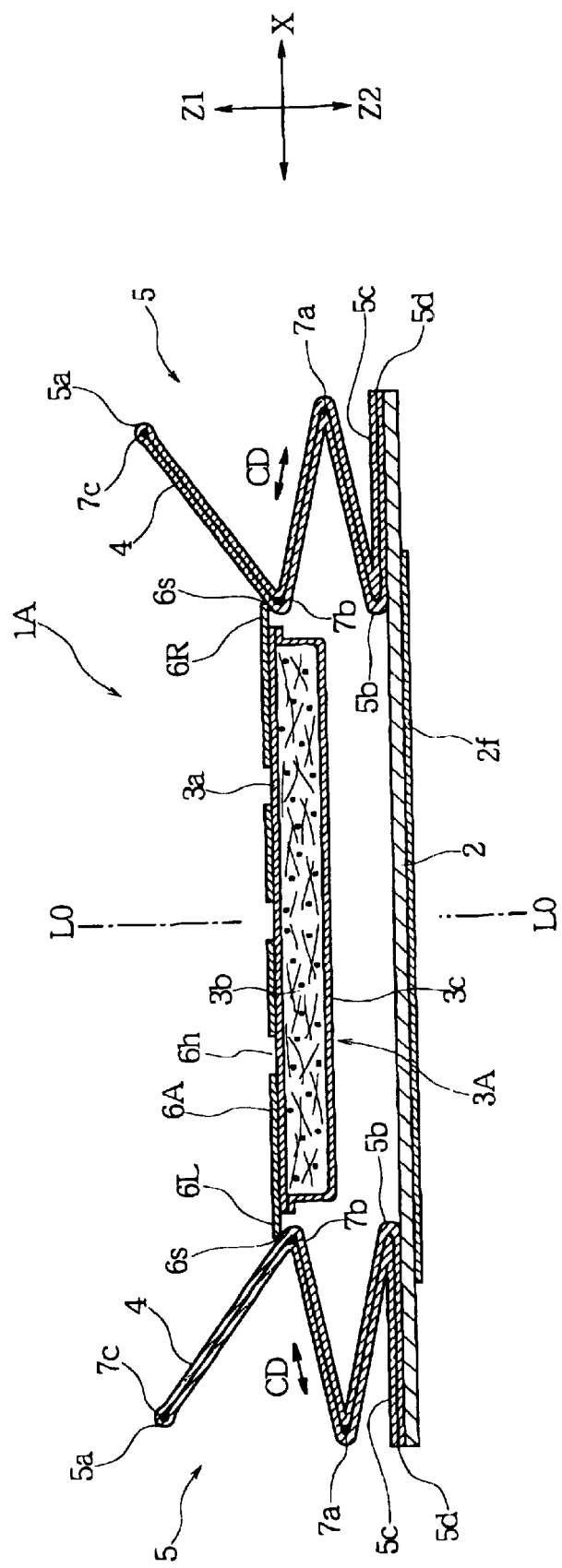
FIG. 11 is a sectional view taken along line XI—XI of FIG. 10.

FIG. 10 is a partially sectioned perspective view, as taken from the liquid-receiving side, of a modification of the sanitary napkin according to the first embodiment, and FIG. 11 is a sectional view taken along line XI—XI of FIG. 10. A sanitary napkin 1A, as shown in FIG. 10, has substantially the same construction as that of the sanitary napkin 1 shown in FIG. 1, except that a plurality of holes 6h for facilitating passage of the liquid waste is provided at the central region of a connecting sheet 6A, and that a liquid absorbing member 3A, as attached to the lower surface of the connecting sheet 6A, is constructed to include: a liquid-permeable layer 3a positioned on the side of the connecting sheet 6A; the liquid-impermeable layer 3c positioned on the side of the support body 2; and the absorbent core 3b sandwiched between the liquid-permeable layer 3a and the liquid-impermeable layer 3c. Therefore, the liquid-permeable layer 3a is exposed to the outside at the holes 6h of the connecting sheet 6A.

The liquid-permeable layer 3a is formed of a spun-bonded nonwoven fabric or a spun-laced nonwoven fabric made of PE fibers, PP fibers, PET fibers or their composite fibers subjected to hydrophilic treatment. Alternatively, an opened resin sheet may be employed to form the liquid-permeable layer 3a.

It should be noted that the liquid absorbing member 3 of FIG. 2 may be employed for this sanitary napkin 1A, in place of the liquid absorbing member 3A. In other words, the liquid-permeable layer 3a may be omitted in the sanitary napkin 1A. In this case, the absorbent sheet of the absorbent core 3b will be exposed from the holes 6h. Alternatively, the liquid absorbing member 3A having the liquid-permeable layer 3a may be employed for the sanitary napkin 1 of FIG. 1, in place of the liquid absorbing member 3.

Figure 12:
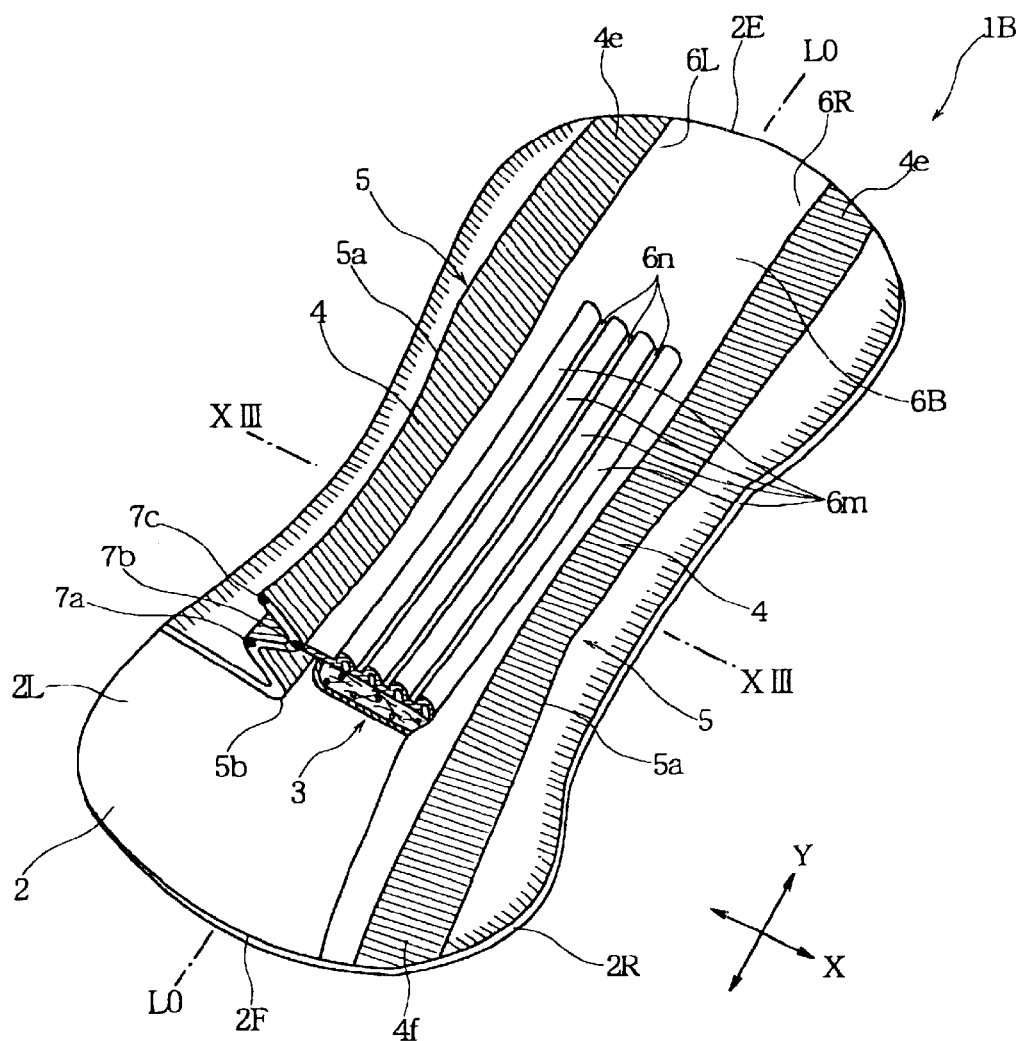
FIG. 12 is a partially sectioned perspective view showing a further modification of the sanitary napkin of the first embodiment.
Figure 13:
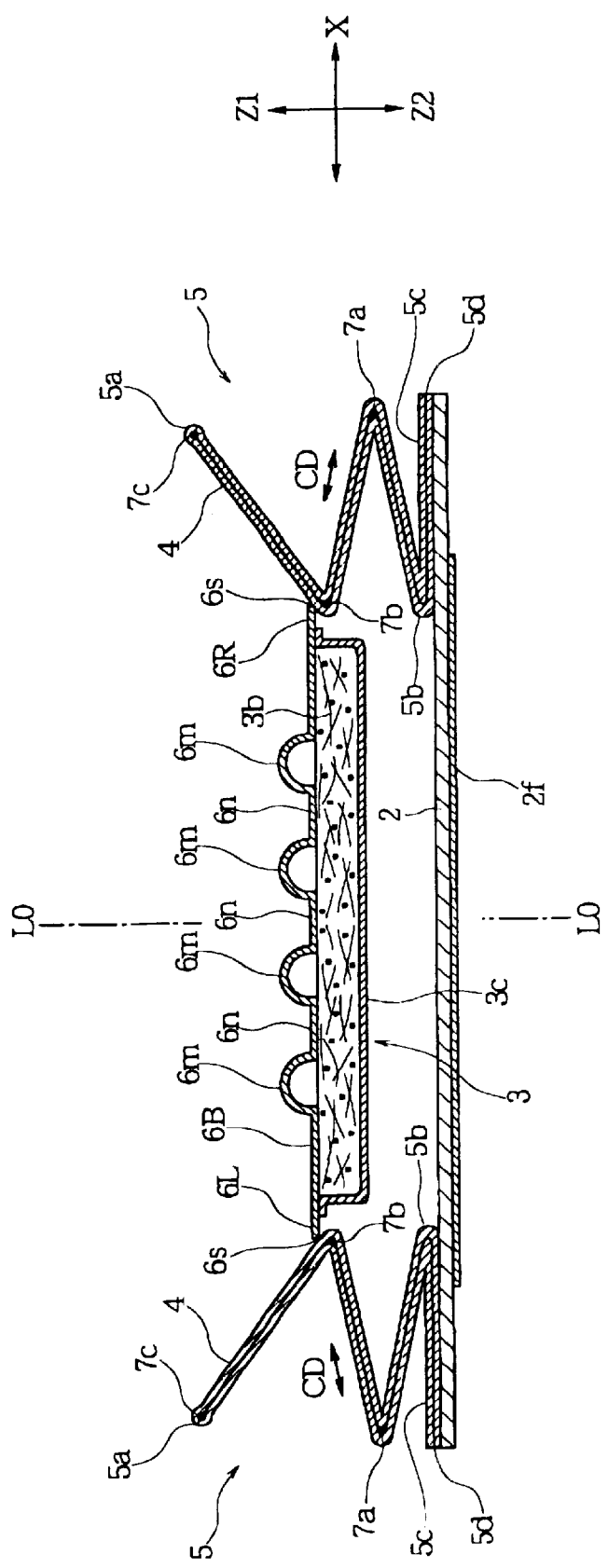
FIG. 13 is a sectional view taken along line XIII—XIII of FIG. 12.

FIG. 12 is a partially sectioned perspective view, as taken from the liquid-receiving side, of another modification of the sanitary napkin according to the first embodiment, and FIG. 13 is a sectional view taken along line XIII—XIII of FIG. 12.

A sanitary napkin 1B, as shown in FIG. 12, has substantially the same construction as that of the sanitary napkin 1 shown in FIG. 1, except that corrugations are formed at the central region of a connecting sheet 6B. These corrugations have ridges 6m and valleys 6n extending in the direction Y and alternating with each other in the direction X. With these corrugations being formed on the liquid-receiving side surface, the liquid waste can be prevented from migrating in the direction X, to cause little sideway leakage. These corrugations of the connecting sheet 6B can be formed by pressing or heat-pressing a sheet similar to the formation of the corrugations of the side walls.

Figure 14:
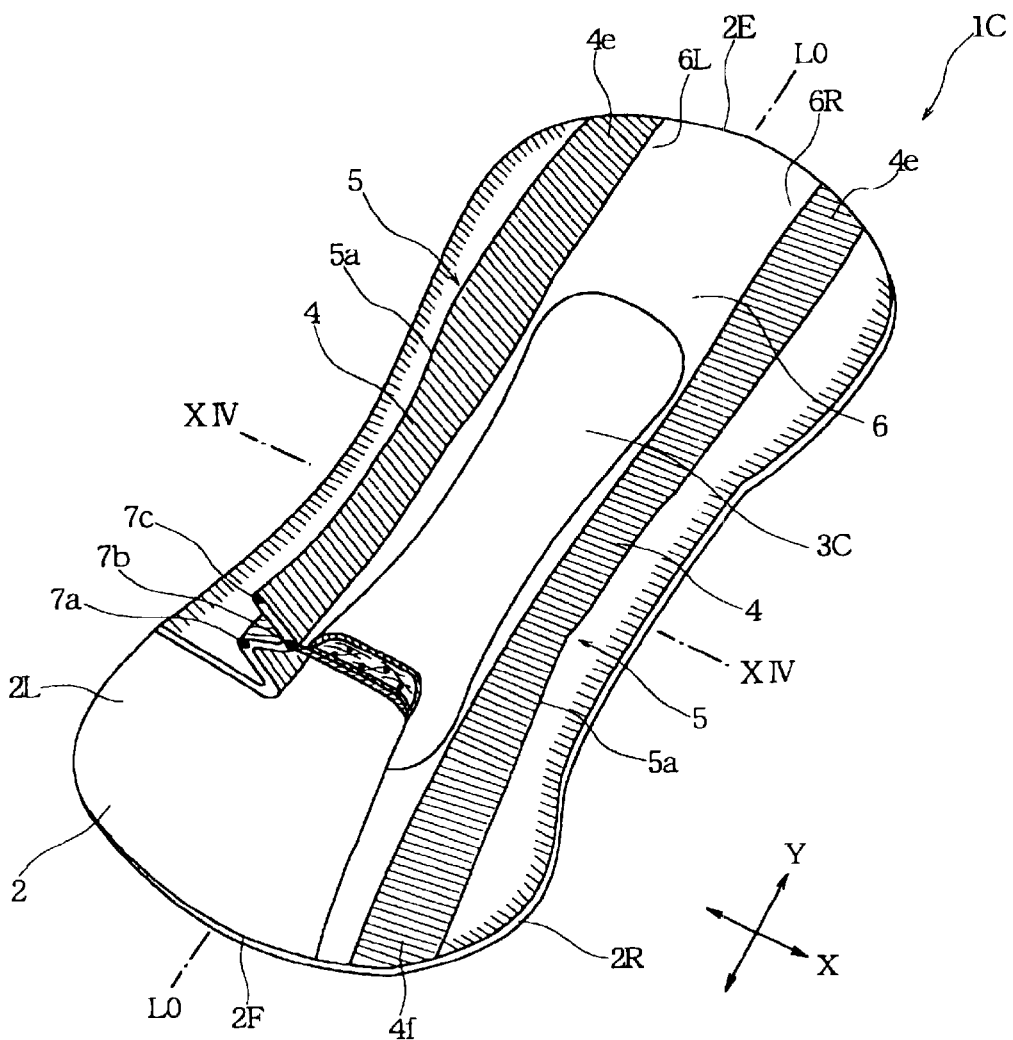
FIG. 14 is a partially sectioned perspective view showing a sanitary napkin as an absorbent article according to a second embodiment of the invention.
Figure 15:
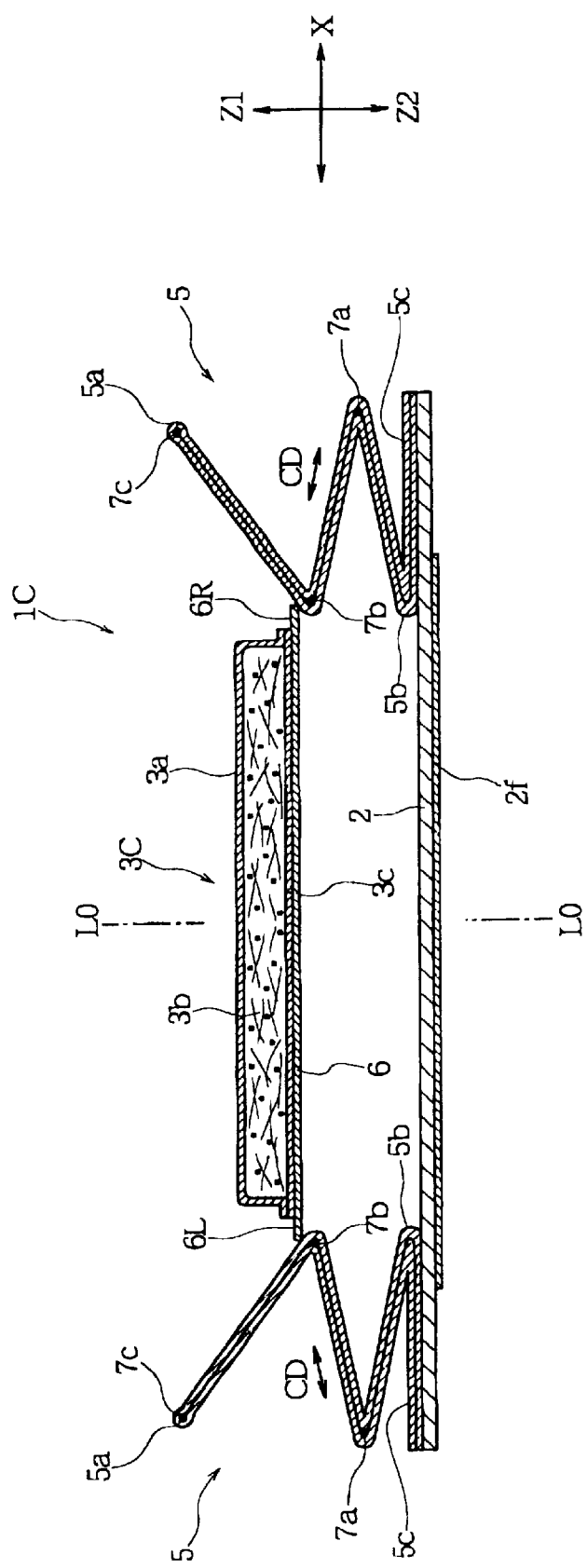
FIG. 15 is a sectional view taken along line XIV—XIV of FIG. 14.
Figure 16:
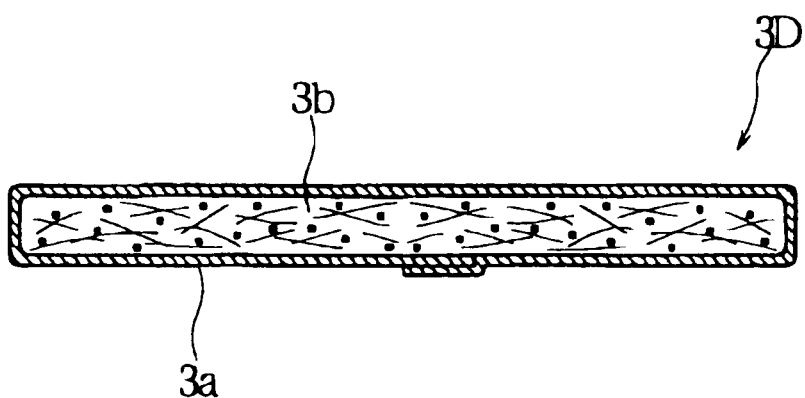
FIG. 16 is a sectional view showing a modification of an absorbent core.

FIG. 14 is a partially sectioned perspective view showing a second embodiment of the invention; FIG. 15 is a sectional view taken along line XIV—XIV of FIG. 14; and FIG. 16 is a sectional view showing a modification of the liquid absorbing member.

A sanitary napkin 1C, as shown in FIG. 14, has substantially the same construction as that of the sanitary napkin 1 of the first embodiment, except that a liquid absorbing member 3C is formed into an hour glass shape and disposed on the liquid-receiving side of the connecting sheet 6. Even if the liquid absorbing member 3C is attached not to the lower surface of the connecting sheet 6, unlike the first embodiment, but to the upper surface of the connecting sheet 6, the liquid absorbing member 3C can exhibit independent behaviors to follow the motions of the wearer as in the first embodiment.

In the sanitary napkin 1C, the liquid absorbing member 3C is disposed on the liquid-receiving side of the connecting sheet 6 which is attached at its two side portions 6R and 6L to the vicinities of the elastic members 7b of the side walls 5. The liquid absorbing member 3C has a structure similar to that of the liquid absorbing member 3A to include: the liquid-permeable layer 3a to confront the wearer; the liquid-impermeable layer 3c to confront the connecting sheet 6; and the absorbent core 3b sandwiched between the liquid-permeable layer 3a and the liquid-impermeable layer 3c. In this structure, the connecting sheet 6 may be either liquid-permeable or liquid-impermeable. The liquid absorbing member 3C may be replaced by a liquid absorbing member 3D which is formed by enveloping the entire surface of the absorbent core 3b by the liquid-permeable layer 3a, as shown in FIG. 16. In this case, the connecting sheet is preferably made liquid-impermeable. Alternatively, the connecting sheet 6 may be made liquid-impermeable, and the liquid absorbing member 3C may be formed only of the absorbent core 3b and the liquid-permeable layer 3a covering the liquid-receiving side surface of the absorbent core 3b, while omitting the liquid-impermeable layer 3c.

For attachment of the liquid absorbing member 3C or 3D to the connecting sheet 6, the adhesive can be applied as in the aforementioned manner, for example, by applying the adhesive in a spiral-, linear- or dotted line-pattern or by spraying the adhesive.

In this second embodiment, it is possible to attach (or join) the liquid absorbing member 3C or 3D to the connecting sheet 6 exclusively in the vicinity of the longitudinally extending center line L0 to thereby leave the two side portions of the liquid absorbing member 3C or 3D unattached. In this structure, since the distance in the direction X from the attached portion between the side walls 5 and the connecting sheet 6 to the attached portion between the liquid absorbing member 3C or 3D and the connecting sheet 6 is so elongated that the motions of the side walls 5 can be absorbed by the connecting sheet 6 more effectively, to thereby allow the liquid absorbing member 3C or 3D to behave more independently of the side walls 5. In this structure, also, the liquid waste having flown to the two side portions 6R and 6L of the connecting sheet 6 can flow to the lower side of the unattached side portions of the liquid absorbing member, i.e., into the clearance between the connecting sheet 6 and the unattached side portions of the liquid absorbing member. Therefore, the liquid absorbing member 3D shown in FIG. 16 is preferably used to absorb the liquid waste having flown to the two side portions 6R and 6L of the connecting sheet 6, from the lower side of the unattached side portions thereof.

Figure 17:
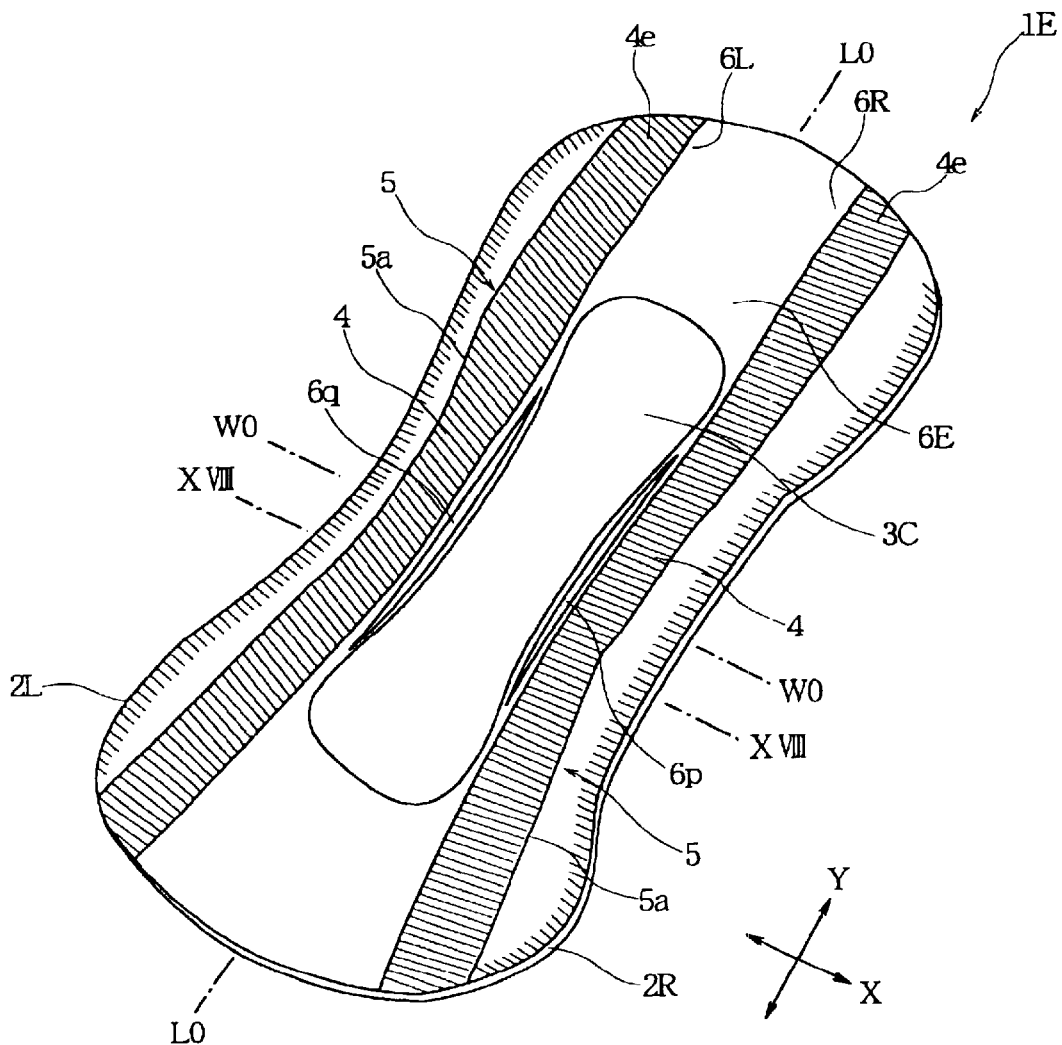
FIG. 17 is a perspective view showing a sanitary napkin as an absorbent article according to a third embodiment of the invention.
Figure 18:
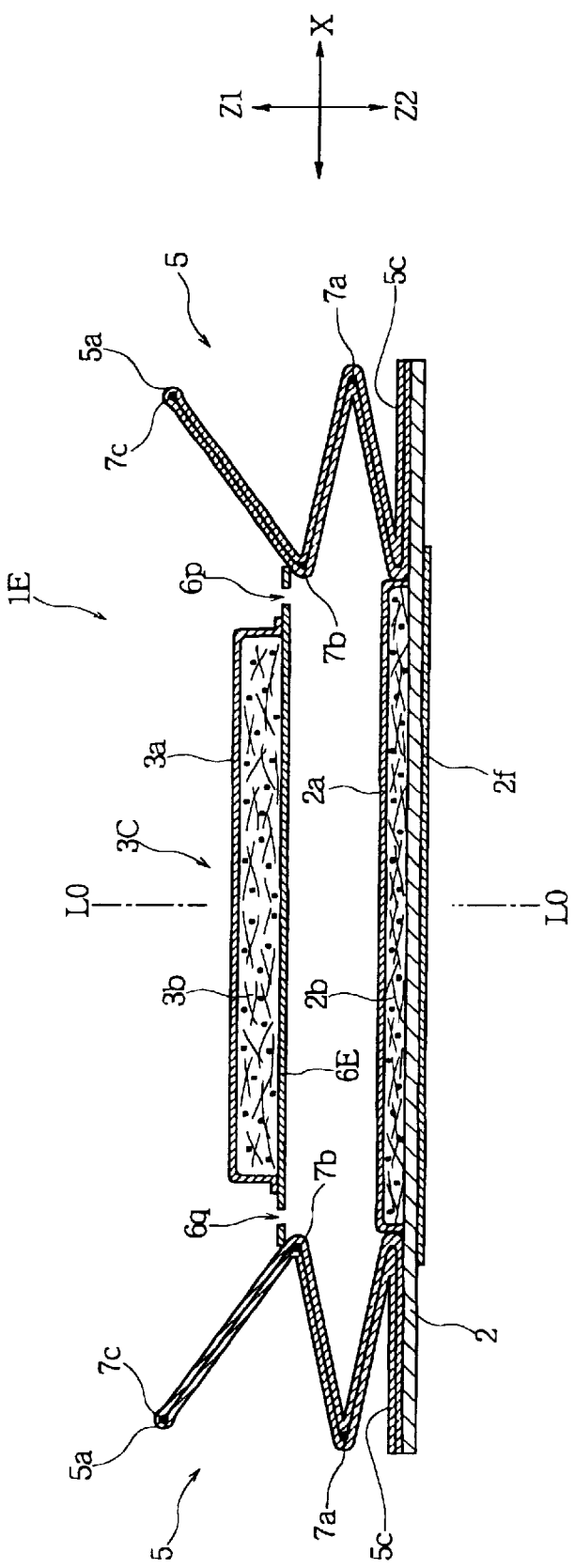
FIG. 18 is a sectional view taken along line XVIII—XVIII of FIG. 17.

FIG. 17 is a perspective view showing a third embodiment of the invention, and FIG. 18 is a sectional view taken along line XVIII—XVIII of FIG. 17. In a sanitary napkin 1E shown in FIG. 17, the liquid absorbing member 3C having the hour glass shape is disposed on the liquid-receiving side of a connecting sheet 6E as in the sanitary napkin 1C of the second embodiment shown in FIG. 14.

In the sanitary napkin 1E, slits 6p and 6q are formed in the two side portions 6R and 6L of the connecting sheet 6E. By using this connecting sheet 6E, the side walls 5 and the connecting sheet 6E are enabled to exhibit independent behaviors at portions where the slits 6p and 6q are formed. Therefore, the liquid absorbing member 3C, as located between the slits 6p and 6q, can follow the deformation of the crotch of the wearer.

In this embodiment, the liquid waste migrates through the slits 6p and 6q to the lower side of the connecting sheet 6E. As shown in FIG. 18, therefore, it is preferable that a second absorber (or absorbing member) other than the liquid absorbing member 3C is disposed on the support body 2 to absorb the liquid waste having passed through the slits 6p and 6q.

In the sanitary napkin 1E, the second absorber includes: a second absorbent core 2b; and a liquid-permeable layer 2a covering the liquid-receiving side of the second absorbent core 2b. The liquid-permeable layer 2a is formed of a spun-bonded or spun-laced nonwoven fabric of fibers subjected to hydrophilic treatment. The second absorbent core 2b is formed, like the absorbent core 3b, by enveloping the pulp or the mixture of the pulp and the SAP with tissue paper or by overlapping sheets of absorbent paper.

Since the liquid absorbing member 3C in the free state can come into close contact with the discharging part of the wearer to absorb and retain the menstrual blood sufficiently, the second absorbent core 2b may be thinner than the liquid absorbing member 3C and can be formed by overlaying sheets of absorbent paper such as tissue paper. This second absorbent core 2b of tissue paper or the like is preferred to have such a larger area than that of the liquid absorbing member 3C as to protrude from the right and left sides of the liquid absorbing member 3C, as viewed from the top. Alternatively, the second absorbent core may be disposed exclusively in the vicinities just under the slits 6p and 6q of the connecting sheet 6E but not in the vicinity of the longitudinally extending center line L0.

Figure 19:
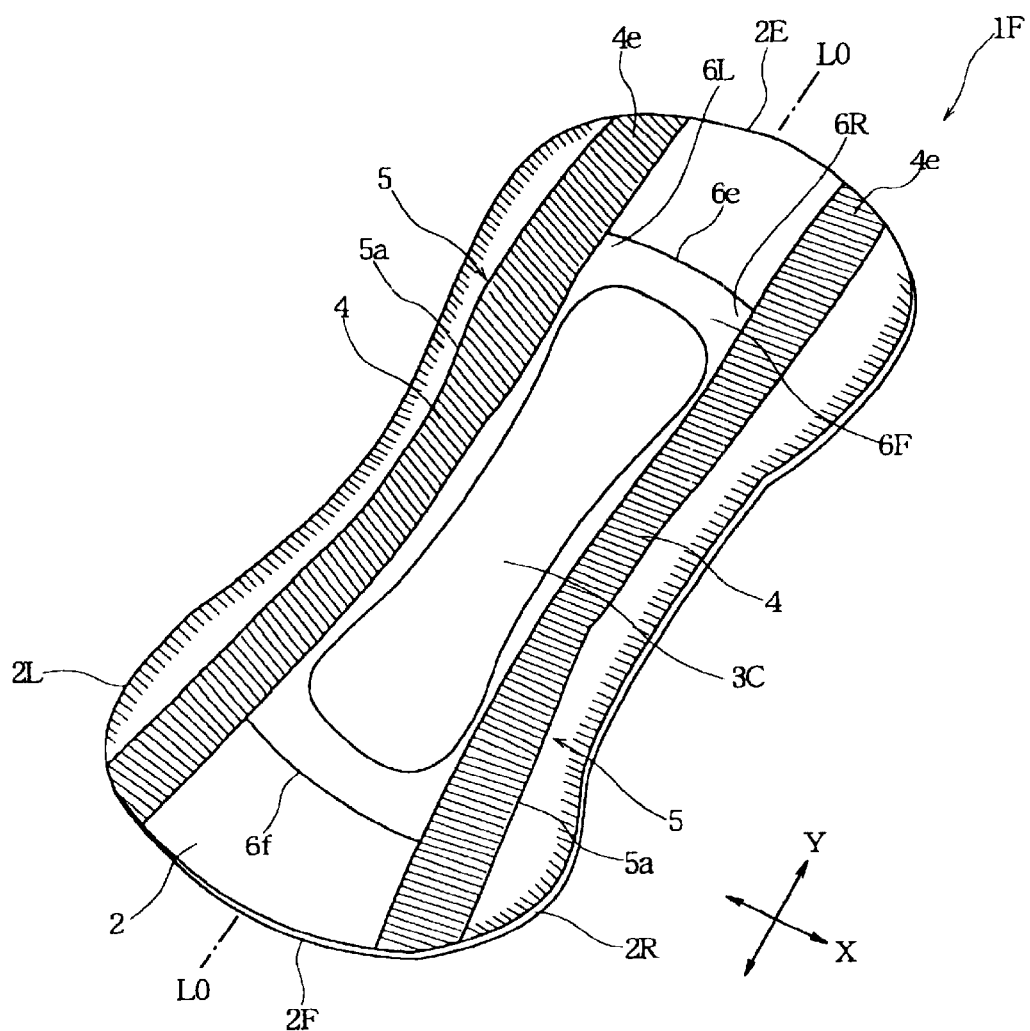
FIG. 19 is a perspective view showing a modification of the sanitary napkin of the third embodiment.
Figure 20:
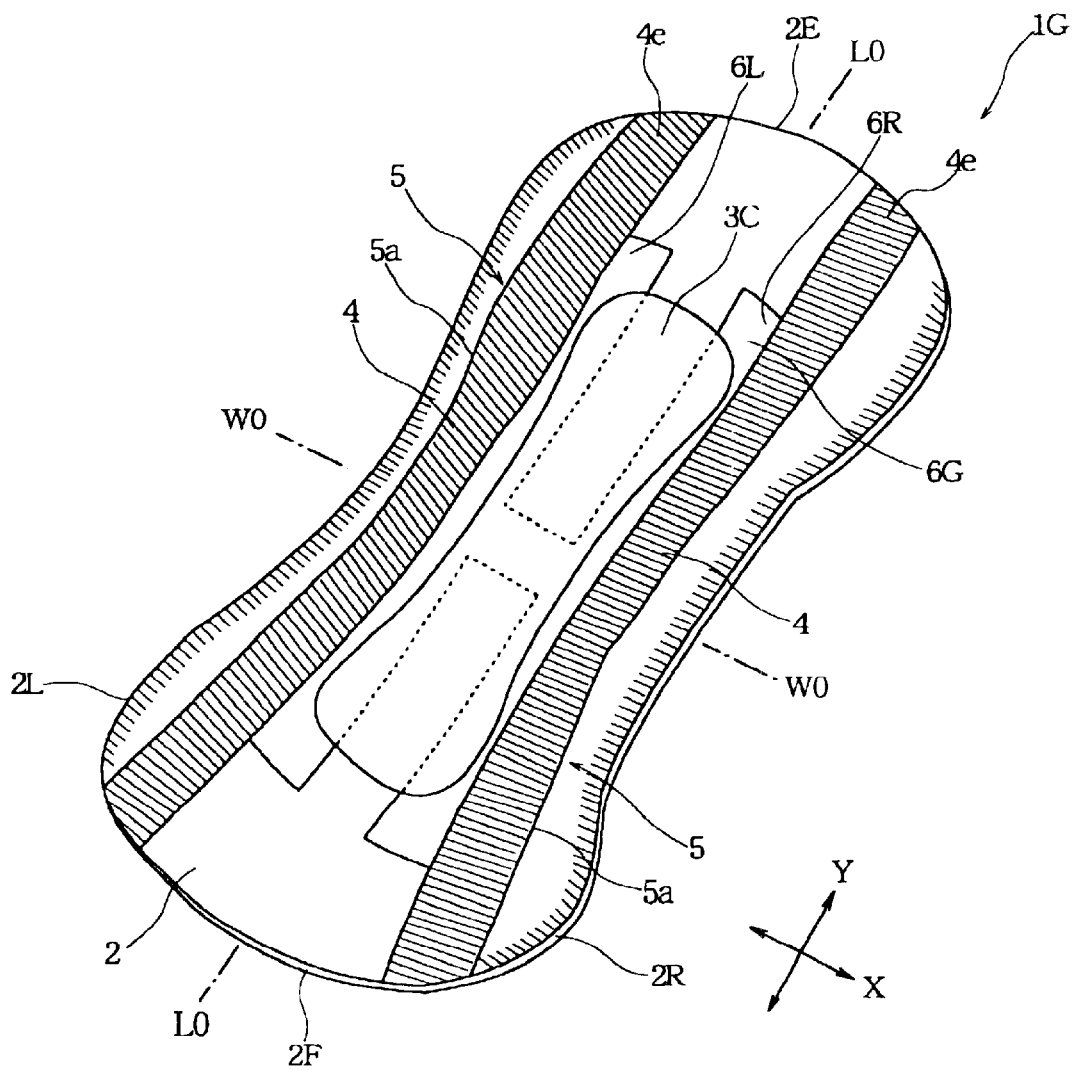
FIG. 20 is a perspective view showing another modification of the sanitary napkin of the third embodiment.
Figure 21:
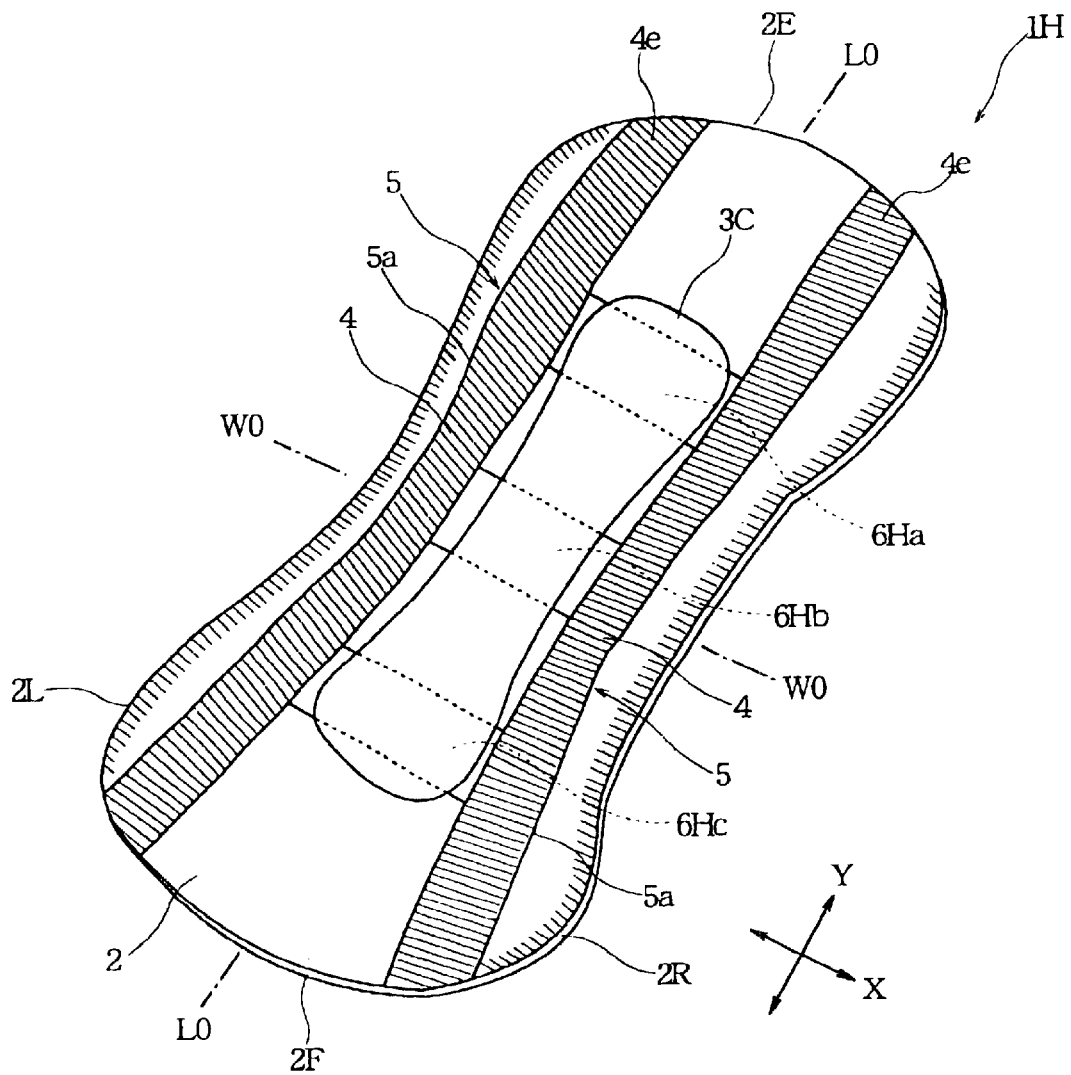
FIG. 21 is a perspective view showing still another modification of the sanitary napkin of the third embodiment.

FIGS. 19, 20 and 21 are perspective views, as taken from the liquid-receiving sides, and individually show modifications of the sanitary napkin according to the third embodiment. A sanitary napkin 1F shown in FIG. 19, a sanitary napkin 1G shown in FIG. 20, and a sanitary napkin 1H shown in FIG. 21 are given substantially the same structure as that of the sanitary napkin 1E shown in FIGS. 17 and 18, excepting the connecting sheet.

In the sanitary napkin 1F of FIG. 19, a connecting sheet 6F having a smaller longitudinal size than that of the support body 2 is attached to the side walls 5 at the central portion of the support body 2 in the direction Y. In this structure, since the connecting sheet 6F is not attached at its end portions 6e and 6f to the support body 2, it receives less influences from the deformation of the support body 2 so that it can exhibit more independent behaviors to follow the motions of the crotch of the wearer.

In the sanitary napkin 1G of FIG. 20, a connecting sheet 6G has a smaller longitudinal size than that of the support body 2, as in the connecting sheet 6F shown in FIG. 19. In the connecting sheet 6G, moreover, the connecting sheet 6G is made extremely small in the longitudinal size at the midway portion (or central portion) in the direction X to have a narrow portion extending along a widthwise extending center line W0 so that it has a general shape of letter "H". In this structure, the right and left side portions of the connecting sheet 6G can move independently so that the liquid absorbing member 3C can follow the motions of the crotch of the wearer better.

In the sanitary napkin 1H shown in FIG. 21, three connecting sheets 6Ha, 6Hb and 6Hc are arranged at intervals in the direction Y and individually attached to the side walls 5. In this structure, these connecting sheets 6Ha, 6Hb and 6Hc can move while receiving less influences from one another so that the liquid absorbing member 3C attached on the connecting sheets 6Ha, 6Hb and 6Hc receives less influences from the deformation of the side walls 5. In this modification, the sanitary napkin 1H is provided with three connecting sheets, but the number of connecting sheets may be two, four or more.

Figure 22:
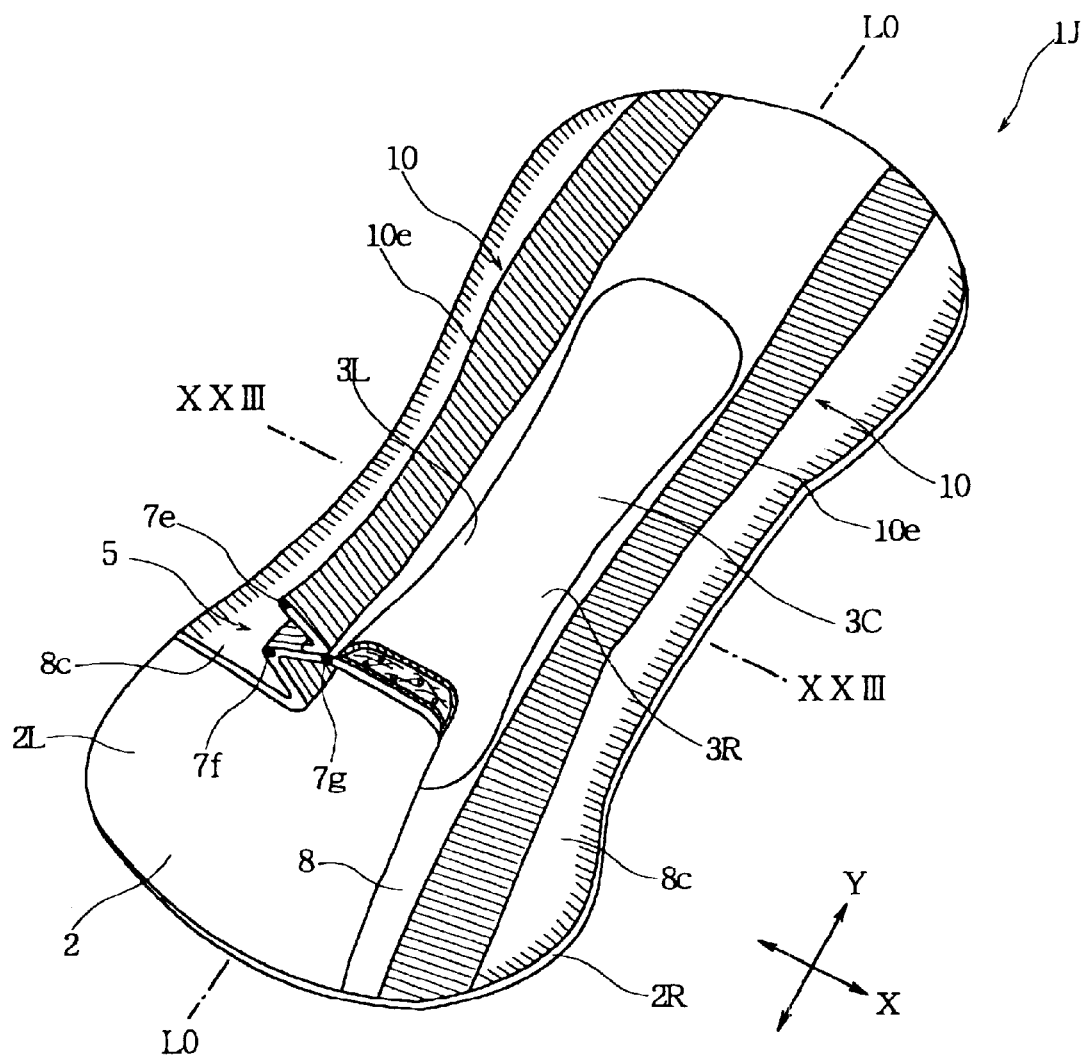
FIG. 22 is a partially sectioned perspective view showing a sanitary napkin as an absorbent article according to a fourth embodiment of the invention.

FIG. 22 is a partially sectioned perspective view showing a fourth embodiment of the invention, and FIG. 23 is a sectional view taken along line XXIII—XXIII of FIG. 22.

In a sanitary napkin 1J shown in FIG. 22, the side wall sheets and the connecting sheet of the first to third embodiments are replaced by one side wall sheet 8 which extends continuously in the direction X from the righthand side portion 2R to the lefthand side portion 2L of the support body 2.

This side-wall sheet 8 is formed with fine wrinkles (or corrugations), like the sidewall sheets 4, which individually extend in the direction X and are repeated in the direction Y. Two wrinkled sheets are laminated to form the side wall sheet 8. Between these two sheets, like the side wall sheets 4, there are sandwiched and attached elastic members 7f, 7g, 7h and 7i in an elongated (or stretched) state. These elastic members 7f, 7g, 7h and 7i are arranged at a predetermined spacing. In this structure, the spacing between the elastic members 7g and 7h is set slightly larger than the widthwise size of the liquid absorbing member 3C. In the state where the sheets clamping the elastic members are stretched, i.e., where the side wall sheet 8 is stretched, the two widthwise side portions of the side wall sheet 8 are attached individually to the two side portions 2R and 2L of the support body 2 to form attachment portions 8c and 8c.

The side wall sheet 8 in an developed state has a larger widthwise size than that of the support body 2, but is folded zigzag, like the side wall sheets 4, along the portions where the elastic members are disposed. As shown in FIG. 23, more specifically, the portions having the elastic members 7f and 7i are directed to the outer sides of the support body 2 in the direction X. Between the elastic members 7g and 7h, the side wall sheet 8 provides a flat portion (or central portion) 8t. The flat portion 8t is spaced away from the support body 2 toward the Z1 side. The liquid absorbing member 3C is attached on the liquid-receiving side of the flat portion 8t to exhibit behaviors independent of the support body 2 as in the first to third embodiments. In the sanitary napkin 1J, therefore, the liquid absorbing member 3C can also follow the motions of the crotch of the wearer.

In the sanitary napkin 1J, moreover, sheets 10s and 10s extending in the direction Y are disposed just on the outer sides of the two side portions 3R and 3L of the liquid absorbing member 3C. It is preferred that the sheets 10s are provided at their free ends 10e with elastic members 7e to form the leakage preventing cuffs with the free ends 10e rising toward the wearer to prevent the leakage in the direction X.

FIG. 24 is a sectional view similar to that of FIG. 23 but shows a modification of the fourth embodiment. In FIG. 24, there is provided a single sheet 10t for forming leakage preventing cuffs 10. The sheet 10t continues in the direction X, and the liquid absorbing member 3C is disposed on the liquid-receiving side of the sheet 10t.

It should be noted that the connecting sheet of the first to third embodiments may be formed like this sheet 10t to form the leakage preventing cuffs.

It should be noted that the second absorbent core may be disposed on the support body 2 also in the first, second and fourth embodiments, as in the third embodiment.

Although the invention has been described on the embodiments in which the absorbent article is exemplified by the sanitary napkin, the invention is also applicable to other kinds of absorbent article such as a diaper, a urine pad or a pantie liner.

According to the invention thus far described in detail, the absorbent core can exhibit behaviors independent of the support body so that the liquid absorbing member can always be held in close contact with the discharging part of the wearer. In this state, moreover, the absorbent core can follow the motions of the wearer so that it can absorb the liquid waste reliably and effectively.

Although various exemplary embodiments have been shown and described, the invention is not limited to the embodiments shown. Therefore, the scope of the invention is intended to be limited solely by the scope of the claims that follow.

What is claimed is:

1. An absorbent article comprising:
   a support body for confronting an external wear;
   a liquid absorbing member positioned on the liquid-receiving side of said support body;
   two side wall sheets disposed on two sides of said support body lying opposite one another in the widthwise direction, the side wall sheets being separated from one another in the widthwise direction and being longitudinally attached at their root ends to said support body; and
   a connecting sheet connecting said two side wall sheets,
   wherein said side wall sheets are individually subjected to elastic shrinking forces in the longitudinal direction for shrinking to raise the free ends thereof from said support body to the liquid-receiving side, and said liquid absorbing member is supported by said connecting sheet so that said liquid absorbing member is movable over said support body while being unattached directly to said support body.

2. The absorbent article as set forth in claim 1,
   wherein said connecting sheet has a stretchability in the longitudinal direction.

3. The absorbent article as set forth in claim 1,
   wherein said liquid absorbing member includes an absorbent core and a liquid-permeable sheet covering at least the liquid-receiving side surface of said absorbent core, and is attached to the liquid-receiving side surface of said connecting sheet.

4. The absorbent article as set forth in claim 1,
   wherein said connecting sheet is liquid-permeable, and said liquid absorbing member is attached to the support body-facing side surface of said connecting sheet.

5. The absorbent article as set forth in claim 1,
wherein longitudinal front and rear end portions of said side wall sheets are wholly attached to said support body to exert forces to curve said support body in the longitudinal direction so that the liquid-receiving side is recessed.

6. The absorbent article as set forth in claim 1,
wherein said side wall sheets are formed with corrugations repeated in the longitudinal direction for exhibiting the elastic shrinking forces in the longitudinal direction.

7. The absorbent article as set forth in claim 1,
wherein elastic members are attached to said side wall sheets for exhibiting the elastic shrinking forces in the longitudinal direction.

8. The absorbent article as set forth in claim 7,
wherein each side wall sheet is provided with a plurality of elastic members extending in the longitudinal direction and arranged at a spacing therebetween from the root end to the free end.

9. The absorbent article as set forth in claim 1,
wherein said side wall sheets extend in a zigzag shape or a corrugated shape from the root ends to the free ends.

10. The absorbent article as set forth in claim 1,
wherein said connecting sheet is attached to said side wall sheets respectively at a position between the free end and the root end, and
wherein said side wall sheets are extended at their free ends farther toward the liquid-receiving side than the attached portions to said connecting sheet so that leakage preventing cuffs are formed of the extensions of said side wall sheets from said attached portions.

11. The absorbent article as set forth in claim 10,
wherein elastic members are attached to the free ends of said side wall sheets for exhibiting elastic shrinking forces in the longitudinal direction.

12. The absorbent article as set forth in claim 1,
wherein another absorbent member is provided on said support body to confront said liquid absorbing member supported by said connecting sheet.

13. An absorbent article comprising:
a support body for confronting an external wear;
a liquid absorbing member positioned on the liquid-receiving side of said support body; and
a side wall sheet having two side portions and a central portion therebetween in the widthwise direction, the side wall sheet connecting two side portions of said support body lying opposite one another in the widthwise direction, with its two side portions being individually attached to the two side portions of said support body but with its central portion being unattached to said support body,
wherein said side wall sheet is subjected to an elastic shrinking force in the longitudinal direction for shrinking to separate its central portion from said support body to the liquid-receiving side, and said liquid absorbing member is supported by the central portion of said side wall sheet so that said liquid absorbing member is movable over said support body while being unattached directly to said support body.

14. The absorbent article as set forth in claim 13,
wherein said side wall sheet has a stretchability in the longitudinal direction.

15. The absorbent article as set forth in claim 13,
wherein said liquid absorbing member includes an absorbent core and a liquid-permeable sheet covering at least the liquid-receiving side surface of said absorbent core, and is attached to the liquid-receiving side surface of the central portion of said side wall sheet.

16. The absorbent article as set forth in claim 13,
wherein said side wall sheet is liquid-permeable, and said liquid absorbing member is attached to the support body-facing side surface of the central portion of said side wall sheet.

17. The absorbent article as set forth in claim 13,
wherein longitudinal front and rear end portions of said side wall sheet are wholly attached to said support body to exert a force to curve said support body in the longitudinal direction so that the liquid-receiving side is recessed.

18. The absorbent article as set forth in claim 13,
wherein said side wall sheet is formed with corrugations repeated in the longitudinal direction for exhibiting the elastic shrinking force in the longitudinal direction.

19. The absorbent article as set forth in claim 13,
wherein elastic members are attached to said side wall sheet for exhibiting. the elastic shrinking force in the longitudinal direction.

20. The absorbent article as set forth in claim 19,
wherein each side portion of the side wall sheet is provided with a plurality of elastic members extending in the longitudinal direction and arranged at a spacing therebetween toward the central portion of the side wall sheet.

21. The absorbent article as set forth in claim 13,
wherein the side portions of said side wall sheet extend in a zigzag shape or a corrugated shape toward the central portion of the side wall sheet.

22. The absorbent article as set forth in claim 13,
wherein leakage preventing cuffs are provided on two widthwise sides of said liquid absorbing member to rise toward the liquid-receiving side.

23. The absorbent article as set forth in claim 13,
wherein another absorbent member is provided on said support body to confront said liquid absorbing member supported by the central portion of said side wall sheet.

* * * * *

UNITED STATES PATENT AND TRADEMARK OFFICE
CERTIFICATE OF CORRECTION

PATENT NO. : 6,458,113 B2
DATED : October 1, 2002
INVENTOR(S) : Masahiro Kashiwagi It is certified that error appears in the above-identified patent and that said Letters Patent is hereby corrected as shown below:

<u>Title page,</u>
Item [73], Assignee, delete "Uni-Chem Corporation" and substitute
-- Uni-Charm Corporation --.

Signed and Sealed this

First Day of April, 2003

JAMES E. ROGAN
*Director of the United States Patent and Trademark Office*